United States Patent [19]
Matsumoto et al.

[11] Patent Number: 5,393,780
[45] Date of Patent: Feb. 28, 1995

[54] 4-FLUOROBIPHENYL DERIVATIVES

[75] Inventors: Masakatsu Matsumoto, Sagamihara; Nobuko Watanabe, Tokyo; Eiko Mori, Tokyo; Miwa Ishihara, Tokyo; Tetsuaki Yamaura, Tokyo; Misao Aoyama, Tokyo; Hiroshi Ikawa, Tokyo; Hisako Kobayashi, Tokyo, all of Japan

[73] Assignee: Fujirebio Inc., Tokyo, Japan

[21] Appl. No.: 217,566

[22] Filed: Mar. 25, 1994

[30] Foreign Application Priority Data

Mar. 26, 1993 [JP] Japan .................... 5-090556

[51] Int. Cl.⁶ .............................. A01N 37/10
[52] U.S. Cl. ..................... 514/543; 514/570; 514/460; 562/469; 560/59; 549/292
[58] Field of Search ............ 560/59; 562/469; 549/292; 514/460, 470, 543

[56] References Cited
U.S. PATENT DOCUMENTS

| | | | |
|---|---|---|---|
| 4,459,422 | 7/1984 | Willard | 560/59 |
| 4,537,906 | 8/1985 | Belanger et al. | 514/532 |
| 4,582,914 | 4/1986 | Volante et al. | 560/59 |
| 4,620,025 | 10/1986 | Sletzinger et al. | 560/59 |
| 4,736,064 | 4/1988 | Baldwin | 560/59 |
| 4,855,321 | 8/1989 | Smith et al. | 514/532 |
| 4,992,429 | 2/1991 | Ullrich et al. | 514/129 |
| 5,001,128 | 3/1991 | Neuenschwander | 514/278 |
| 5,166,171 | 11/1992 | Jendralla et al. | 560/59 |

Primary Examiner—Paul J. Killos
Attorney, Agent, or Firm—Oblon, Spivak, McClelland, Maier, & Neustadt

[57] ABSTRACT

A 4-fluorobiphenyl derivative of formula (I):

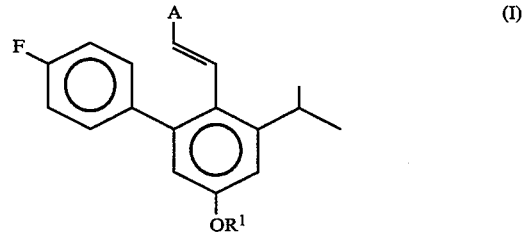

wherein A is a ω-oxycarbonyldihydroxybutyl group of formula (II):

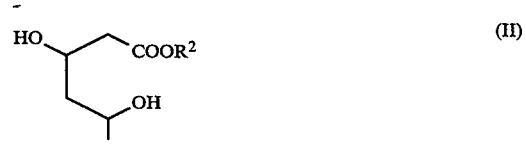

wherein $R^2$ is a hydrogen atom, an alkyl group, an alkaline metal or an alkaline earth metal; a tetrahydropyranyl group of formula (III):

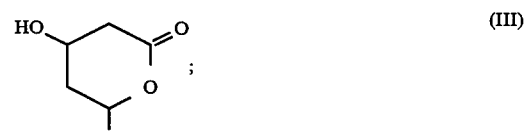

or a ω-oxycarbonyl-3-oxobutyl group of formula (IV):

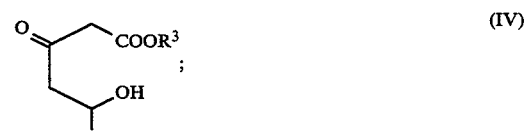

wherein $R^3$ is an alkyl group; $R^1$ is an alkyl group. This 4-fluorobiphenyl derivative is useful as an effective component for a cholesterol or lipid lowering agent.

18 Claims, No Drawings

4-FLUOROBIPHENYL DERIVATIVES

BACKGROUND OF THE INVENTION

1. Field of the Invention

The present invention relates to a 4-fluorobiphenyl derivative of formula (I), which is useful as a cholesterol lowering agent or a lipid lowering agent because of its strong inhibitory effect on a 3-hydroxy-3-methylglutaryl-coenzyme A reductase (hereinafter referred to as HMG-CoA reductase) thereof:

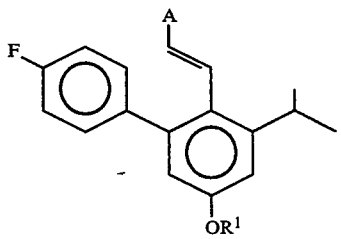

wherein A is a ω-oxycarbonyldihydroxybutyl group of formula (II):

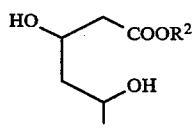

wherein $R^2$ is a hydrogen atom, an alkyl group having 1 to 6 carbon atoms, which may have a substituent, an alkaline metal or an alkaline earth metal; or a tetrahydropyranyl group of formula (III):

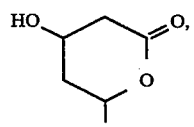

$R^1$ is an alkyl group having 1 to 6, substituted with a heteroaromatic group, an alkoxyalkyl group, or a hydroxyalkyl group.

2. Discussion of Background

ML-236B (Mevastatin) has been discovered in the form of a fungal metabolite, which is a compound capable of lowering the concentration of cholesterol in the blood, which is considered to be a prominent factor for causing arteriosclerosis (refer to Japanese Laid-Open Patent Application 50-155690). ML-236B, however, has not yet been clinically used.

The effect of lowering the concentration of cholesterol in the blood exhibited by ML-236B is based on its competitive inhibitory effect on HMG-CoA reductase which serves as a rate-determining enzyme for the biosynthesis of cholesterol.

ML-236B is a compound constructed in such a manner that a hexahydronaphthalene skeleton is bonded to the ω-position of 3,5-dihydroxyheptanoic acid, and it is understood that the 3,5-dihydroxyheptanoic moiety is an indispensable moiety for the generation of the inhibitory effect on the HMG-CoA Reductase.

After the discovery of ML-235B, compounds such as prevastatin (refer to Japanese Laid-Open Patent Application 57-2240), simvastatin (refer to U.S. Pat. No. 4,444,784)) and lovastatin (refer to U.S. Pat. No. 4,231,938) have been discovered and are used clinically in practice. These compounds are considered as such compounds that substituents of the hexahydronaphthalene ring of ML-236B are partially modified biochemically or chemically.

Furthermore, varieties of compounds have been synthesized in an attempt to obtain compounds having higher HMG-CoA reductase inhibitory effect than those of drugs such as pravastatin, simvastatin, and lovastatin, for instance, as disclosed in Japanese Laid-Open Patent Application 56-45470, U.S. Pat. No. 4,375,475, Japanese Laid-Open Patent Application 58-8076, U.S. Pat. Nos. 4,459,422, 4,710,513, 4,567,289, 4,812,583, and German Laid-Open Patent 3909278.

The above-mentioned simvastatin and lovastatin exhibit a strong cholesterol lowering effect. However, it has been reported that these compounds also exhibit side effects such as myositis and sleep disorder (refer to Am. J. Cardiol., 62, 28J(1988); 66, 11B(1990); 65, 23F(1988); N. Eng. J. Med., 319(18)1222(1988); Br. Med. J., 30, 669(1990)).

It is considered that one of the factors for causing such side effects is the organotropism of these drugs. To be more specific, pravastatin, which is highly water-soluble, is not incorporated into histoblasts other than those of liver. In contrast to this, simvastatin and lovastatin which are highly lipid-soluble are transferred into both liver cells and non-liver cells, so that myositis and sleep disorder are caused.

It is recognized that simvastatin has an advantage over pravastatin that it has an antiarteriosclerosis effect because of its cytostatic function with respect to the cells of smooth muscles.

In view of these facts, a new HMG-CoA reductase inhibiting agent having an appropriate water-solubility, which is positioned between the two opposite extreme water-solubilities of simvastatin (lovastatin) and pravastatin is desired.

With respect to varieties of compounds which have been synthesized after the development of pravastatin, simvastatin, and lovastatin, their water-solubility and lipid-solubility upon which the generation of the previously mentioned side effects depends, have not been studied.

A compound which can be satisfactorily used as an effective component for a cholesterol lowering agent or a lipid lowering agent has not yet been discovered.

SUMMARY OF THE INVENTION

It is therefore an object of the present invention to provide a compound which exhibits a strong inhibitory effect on HMG-CoA reductase and therefore is useful as a cholesterol lowering agent or a lipid lowering agent, from which the shortcomings of conventional drugs have been eliminated in view of the factors which causes the conventional side effects, that is, factors such as the organotropism and inappropriate water solubility thereof.

This object of the present invention is achieved by a 4-fluorobiphenyl derivative of the following formula (I):

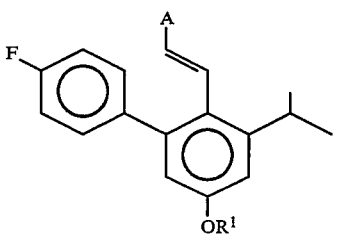
(I)

wherein A is a ω-oxycarbonyldihydroxybutyl group of formula (II):

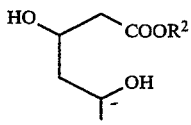
(II)

wherein R² is a hydrogen atom, an alkyl group having 1 to 6 carbon atoms, which may have a substituent, an alkaline metal or an alkaline earth metal; or a tetrahydropyranyl group of formula (III):

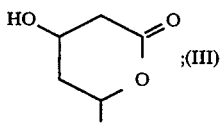
;(III)

R¹ is an alkyl group having 1 to 6 carbon atoms, substituted with a heteroaromatic group, an alkoxyalkyl group, or a hydroxyalkyl group.

DESCRIPTION OF THE PREFERRED EMBODIMENTS

In a 4-fluorobiphenyl derivative of formula (I) of the present invention, A is a ω-oxycarbonyldihydroxybutyl group of formula (II):

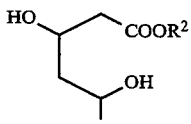
(II)

wherein R² is a hydrogen atom, an alkyl group having 1 to 6 carbon atoms, which may have a substituent, an alkaline metal or an alkaline earth metal.

The alkyl group represented by R² is a straight or branched alkyl group having 1 to 6 carbon atoms, preferably an alkyl group having 1 to 4 carbon atoms, such as methyl group, ethyl group, n-propyl group, isopropyl group, n-butyl group, sec-butyl group, t-butyl group, pentyl group and hexyl group.

Specific examples of the alkaline metal represented by R₄ include potassium, and sodium, and specific examples of the alkaline earth metal represented by R² include calcium and barium. These alkaline metals and alkaline earth metals can usually from salts in combination with carboxyl group.

R¹ is an alkyl group having 1 to 6 carbon atoms, substituted with a heteroaromatic group, an alkoxyalkyl group, or a hydroxyalkyl group.

Examples of a heteroaromatic group with which the alkyl group is substituted include a furyl group, a pyridyl group and a thienyl group.

The alkyl group represented by R¹ is the same as represented by R².

Specific examples of the alkyl group substituted with the heteroaromatic group include furfuryl group, thienylmethyl group, 2-pyridylmethyl group, 3-pyridylmethyl group, 4-pyridylmethyl group, furylethyl group, thienylethyl group, 2-pyridylethyl group, 3-pyridylethyl group, 4-pyridylethyl group, and 2-pridylpropyl group.

Specific examples of the alkoxyl group of the alkoxyalkyl group include methoxy group, ethoxy group, propoxy group, methoxymethoxy group, and methoxyethoxy group.

Specific examples of the alkyl group are the same as the specific examples of the alkyl group represented by R².

Specific examples of the alkoxyalkyl group include methoxymethyl group, methoxyethyl group, methoxypropyl group, ethoxyethyl group, ethoxypropyl group, methoxymethoxyethyl group, methoxyethoxyethyl group, and 2-tetrahydropyranyloxyethyl group.

Specific examples of the hydroxyalkyl group include hdyroxyethyl group, 2-hydroxypropyl group, and 3-hydroxypropyl group.

Of the 4-fluorobiphenyl derivative of formula, the following 4-fluorobiphenyl derivative of formula (IA) is particularly useful in the present invention:

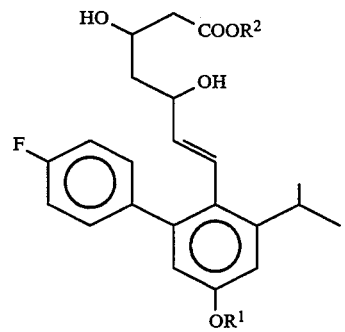

wherein R¹ is an alkyl group having 1 to 6 carbon atoms, which may have a substituent selected from the group consisting of a heteroaromatic group, an alkoxyl group having 1 to 6 carbon atoms, and a hydroxyl group; and R² is an alkaline metal.

Furthermore, a cholesterol or lipid lowering agent which comprises the 4-fluorobiphenyl derivative of the above-mentioned formula (IA) or a 4-fluorobiphenyl derivative of the following formula (IB) as an effective component is particularly effective:

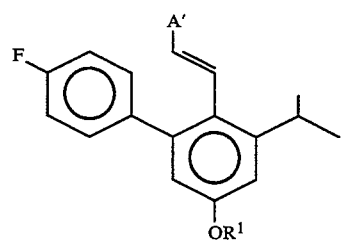

wherein A' is a ω-oxycarbonyldihydroxybutyl group of formula (II):

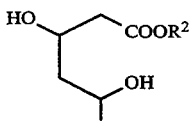

wherein $R^2$ is a hydrogen atom, an alkyl group having 1 to 6 carbon atoms, which may have a substituent, an alkaline metal or an alkaline earth metal; a tetrahydropyranyl group of formula (III):

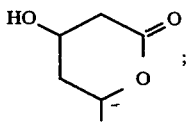

$R^1$ is an alkyl group having 1 to 6 carbon atoms, which may have a substituent selected from the group consisting of a heteroaromatic group, an alkoxyl group having 1 to 6 carbon atoms, and a hydroxyl group.

Specific examples of the 4-fluorobiphenyl derivative represented by formula (I) are as follows:

Sodium (E)-7-[4'-fluoro-5-(2-hydroxyethoxy)-3-(propan-2-yl)biphenyl-2-yl]-3,5-dihydroxy-6-heptenoate,
Sodium (E)-7-[4'-fluoro-5-(2-methoxyethoxy)-3-(propan-2-yl)biphenyl-2-yl]-3,5-dihydroxy-6-heptenoate,
Sodium (E)-7-[4'-fluoro-5-[2-(2-methoxyethoxy)ethoxy]-3-(propan-2-yl)biphenyl-2-yl]-3,5-dihydroxy-6-heptenoate,
Sodium (E)-7-[4'-fluoro-3-(propan-2-yl)-5-(2-pyridylmethyloxy)biphenyl-2-yl]-3,5-dihydroxy-6-heptenoate,
Sodium (E)-7-[4'-fluoro-3-(propan-2-yl)-5-(3-pyridylmethyloxy)bipheny-2-yl]-3,5-dihydroxy-6-heptenoate,
Sodium (E)-7-[4'-fluoro-3-(propan-2-yl)-5-(4-pyridylmethyloxy)biphenyl-2-yl]-3,5-dihydroxy-6-heptenoate,
Sodium (E)-7-[4'-fluoro-3-(propan-2-yl)-5-[2-(pyridyl-2-yl)ethyloxy]biphenyl-2-yl]-3,5-dihydroxy-6-heptenoate,
Sodium (E)-7-[4'-fluoro-3-(propan-2-yl)-5-(2-thienylmethyloxy)biphenyl-2-yl]-3,5-dihydroxy-6-heptenoate,
Sodium (E)-7-[4'-fluoro-3-(propan-2-yl)-5-(3-thienylmethyloxy)biphenyl-2-yl]-3,5-dihydroxy-6-heptenoate,
Sodium (E)-7-[4'-fluoro-5-(3-furylmethyloxy)-3-(propan-2-yl)biphenyl-2-yl]-3,5-dihydroxy-6-heptenoate,
Sodium (E)-7-[4'-fluoro-5-furfuryloxy-3-(propan-2-yl)biphenyl-2-yl]-3,5-dihydroxy-6-heptenoate,
Ethyl (E)-7-[4'-fluoro-5-(2-hydroxyethoxy)-3-(propan-2-yl)biphenyl-2-yl]-3,5-dihydroxy-6-heptenoate,
Ethyl (E)-7-[4'-fluoro-5-(2-methoxyethoxy)-3-(propan-2-yl)biphenyl-2-yl]-3,5-dihydroxy-6-heptenoate,
Ethyl (E)-7-[4'-fluoro-5-[2-(2-methoxyethoxy)ethoxy]-3-(propan-2-yl)biphenyl-2-yl]-3,5-dihydroxy-6-heptenoate,
Ethyl (E)-7-[4'-fluoro-3-(propan-2-yl)-5-(2-pyridylmethyloxy)biphenyl-2-yl]-3,5-dihydroxy-6-heptenoate,
Ethyl (E)-7-[4'-fluoro-3-(propan-2-yl)-5-(3-pyridylmethyloxy)biphenyl-2-yl]-3,5-dihydroxy-6-heptenoate,
Ethyl (E)-7-[4'-fluoro-3-(propan-2-yl)-5-(4-pyridylmethyloxy)biphenyl-2-yl]-3,5-dihydroxy-6-heptenoate,
Ethyl (E)-7-[4'-fluoro-3-(propan-2-yl)-5-[2-(pyridyl-2-yl)ethyloxy]biphenyl-2-yl]-3,5-dihydroxy-6-heptenoate,
Ethyl (E)-7-[4'-fluoro-3-(propan-2-yl)-5-(2-thienylmethyloxy)biphenyl-2-yl]-3,5-dihydroxy-6-heptenoate,
Ethyl (E)-7-[4'-fluoro-3-(propan-2-yl)-5-(3-thienylmethyloxy)biphenyl-2-yl]-3,5-dihydroxy-6-heptenoate,
Ethyl (E)-7-[4'-fluoro-5-(3-furylmethyloxy)-3-(propan-2-yl)biphenyl-2-yl]-3,5-dihydroxy-6-heptenoate,
Ethyl (E)-7-[4'-fluoro-5-furfuryloxy-3-(propan-2-yl)biphenyl-2-yl]-3,5-dihydroxy-6-heptenoate,
trans-(±)-6-[(E)-2-[4'-fluoro-5-(2-hydroxyethoxy)-3-(propan-2-yl)biphenyl-2-yl]ethenyl]-4-hydroxytetrahydropyran-2-one,
trans-(±)-6-[(E)-2-[4'-fluoro-5-(2-methoxyethoxy)-3-(propan-2-yl)biphenyl-2-yl]ethenyl]-4-hydroxytetrahydropyran-2-one,
trans-(±)-6-[(E)-2-[4'-fluoro-5[2-(2-methoxyethoxy)ethoxy]-3-(propan-2-yl)biphenyl-2-yl]ethenyl]-4-hydroxytetrahydropyran-2-one,
trans-(±)-6-[(E)-2-[4'-fluoro-3-(propan-2-yl)-5-(2-pyridylmethyloxy)biphenyl-2-yl]ethenyl]-4-hydroxytetrahydropyran-2-one,
trans-(±)-6-[(E)-2-[4'-fluoro-3-(propan-2-yl)-5-(3-pyridylmethyloxy)biphenyl-2-yl]ethenyl]-4-hydroxytetrahydropyran-2-one,
trans-(±)-6-[(E)-2-[4'-fluoro-3-(propan-2-yl)-5-(4-pyridylmethyloxy)biphenyl-2-yl]ethenyl]-4-hydroxytetrahydropyran-2-one,
trans-(±)-6-[(E)-2-[4'-fluoro-3-(propan-2-yl)-5-(2-pyridyl-2-yl)ethyloxy]biphenyl-2-yl]ethenyl]-4-hydroxytetrahydropyran-2-one,
trans-(±)-6-[(E)-2-[4'-fluoro-3-(propan-2-yl)-5-(2-thienylmethyloxy)biphenyl-2-yl]ethenyl]-4-hydroxytetrahydropyran-2-one,
trans-(±)-6-[(E)-2-[4'-fluoro-3-(propan-2-yl)-5-(3-thienylmethyloxy)biphenyl-2-yl]-4-hydroxytetrahydropyran-2-one,
trans-(±)-6-[(E)-2-[4'-fluoro-5-(3-furylmethyloxy)-3-(propan-2-yl)biphenyl-2-yl]ethenyl]-4-hydroxytetrahydropyran-2-one, and
trans-(±)-6-[(E)-2-[4'-fluoro-5-furfuryloxy-3-(propan-2-yl)biphenyl-2-yl]ethenyl]-4-hydroxytetrahydropyran-2-one.

The 4-fluorobiphenyl derivative of formula (I) of the present invention can be produced in accordance with the following reaction scheme:

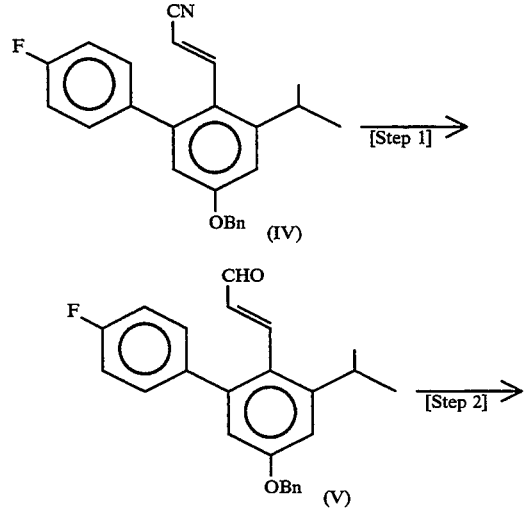

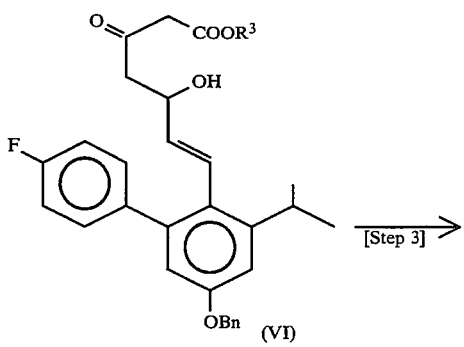
(VI)

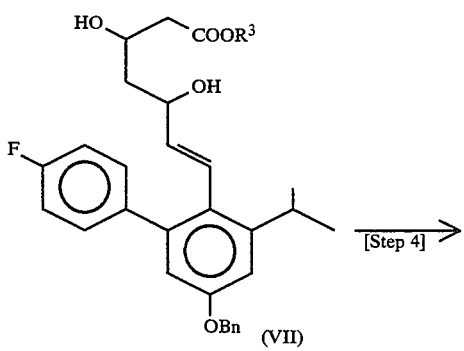
(VII)

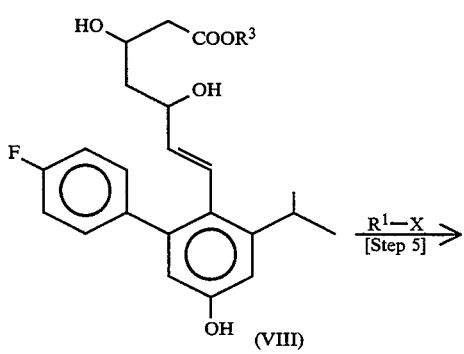
(VIII)

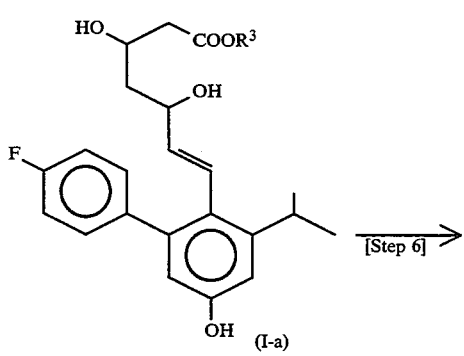
(I-a)

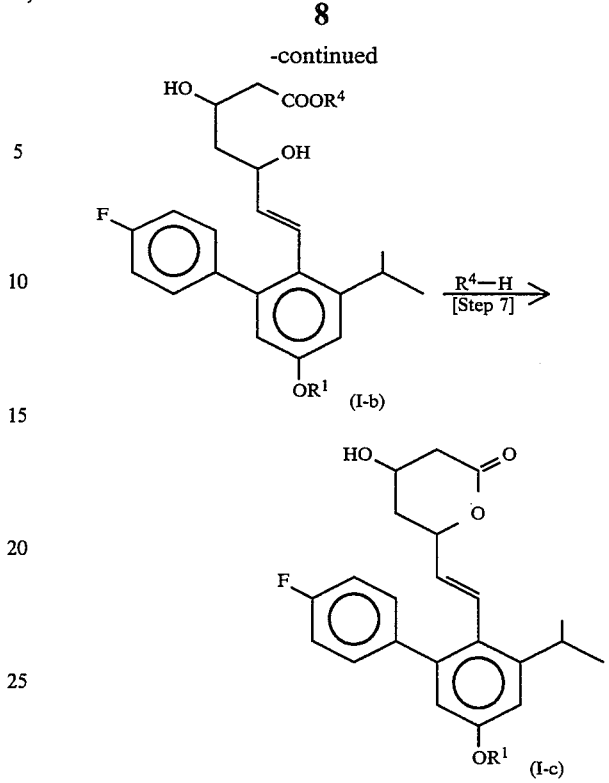
(I-b)

(I-c)

wherein $R^1$ is the same as defined previously, $R^3$ is an alkyl group having 1 to 6 carbon atoms, which may have a substituent, $R^4$ is a hydrogen atom, an alkaline metal, or an alkaline earth metal, and Bn is benzyl group.

Step 1

In this step, an aldehyde derivative of formula (V) is produced by reducing a cyano derivative of formula (IV).

As a reducing agent employed in this reaction, any reducing agents which are capable of reducing cyano group to aldehyde group, for example, diisobutylaluminum hydride (DIBAL), can be employed. The reaction can be carried out in an inert solvent by methods which are conventionally known to those skilled in the art.

The cyano derivative of formula (IV) can be produced by using a 2-biphenylcarboaldehyde derivative as a starting material in accordance with Horner-Emmons Reaction or Wittig Reaction, both of which are conventionally known to those skilled in the art.

Step 2

In this step, a keto-ester derivative of formula (VI) is produced by allowing the aldehyde derivative of formula (V) to react with an acetoacetate.

Examples of the acetoacetate for use in this reaction include methyl acetoacetate, ethyl acetoacetate, propyl acetoacetate, and butyl acetoacetate.

As a base for deriving a dianinon of such an acetoacetate, for example, sodium hydride and butyllithium can be employed.

It is preferable that the reaction be carried out in an atmosphere of an inert gas, in a solvent, for instance, an inert solvent, for examples, ethers such as diethyl ether, tetrahydrofuran (THF), dioxane, and 1,2-dimethoxyethane (DME). These solvents can be used alone or in combination.

The reaction can be carried out at a temperature in the range of −78° C. to room temperature.

Step 3

In this step, a 3,5-dihydroxyheptenoic acid derivative of formula (VII) is produced by reducing the keto-ester derivative of formula (VI) obtained in Step 2. A variety of reducing agents can be employed for the reduction of the carbonyl group in this step. For instance, sodium borohydride can be employed.

Such a reducing agent is employed in an amount in the range of 1 to 6 equivalents to one equivalent of the keto-ester derivative of formula (VI), but for more efficient synthesis of the keto-ester derivative of formula (IV), it is preferable that the amount of such a reducing agent be in the range of 1 to 4 equivalents to one equivalent of the keto-ester derivative of formula (VI).

For improving the steroselectivity in this step, the reaction can be carried out with the addition of a trialkylborane such as trimethylborane, and triethylborane, and pivalic acid to the reaction system in this step.

The reaction is usually carried out in an inert solvent. Examples of an inert solvent for use in this reaction include water, alcohols such as methanol, ethanol, and butanol; ethers such as THF, and dioxane; halogenated hydrocarbons such as methylene chloride, and 1,2-dichloroethane; and aromatic hydrocarbons such as benzene and tolune. These inert solvents can be used alone or in combination.

The reaction can be usually carried out at temperatures in the range of −78° C. to room temperature.

Step 4

In this step, a phenol derivative of formula (VIII) is produced by subjecting the 3,5-dihydroxyheptenoic acid derivative of formula (VII) obtained in Step 3 to catalytic reduction.

It is preferable that the catalytic reduction in this step be such that the double bond in the 3,5-dihydroxyheptenoic acid derivative of formula (VII) be not reduced. Thus, it is preferable to use, for instance, $H_2$/Lindlar's catalyst, and $HCO_2H$, $NEt_3$/Pd-C catalysts.

The reaction is usually carried out in a solvent, for examples, alcohols such as methanol, ethanol and propanol; esters such as methyl acetate, and ethyl acetate; and acetic acid. These solvents can be used alone or in combination.

Step 5

In this step, a 4-fluorobiphenyl derivative of formula (I-a) is produced by allowing the phenol derivative of formula (VIII) obtained in Step 4 to react with a compound of formula $R^1$—X.

In the compound of formula $R^1$—X employed in this step, X is, for instance, a halogen atom such as chlorine, bromine, and iodine; or a substituted sulfonyloxy group such as a methanesulfonyloxy group, and a p-toluenesulfonyloxy group.

In this step, the compound of formula $R^1$—X is used in an amount in the range of 1 to 10 equivalents to one equivalent of the phenol derivative of formula (VIII), preferably in an amount in the range of 1 to 3 equivalents to one equvalent of the phenol derivative of formula (VIII) for the effective synthesis of the 4-fluorobiphenyl derivative of formula (I-a).

It is preferable that the reaction in this step be carried out in the presence of a base such as potassium carbonate, sodium carbonate, sodium hydroxide, potassium hydroxide, and sodium hydride.

Furthermore, it is preferable that the reaction be carried out in an inert solvent. Examples of an inert solvent for use in this reaction include ketones such as acetone and methyl ethyl ketone; ethers such as diethyl ether, THF, dioxane, and DME; and dimethylformamide (DMF). These solvents can be used alone or in combination.

The reaction can be carried out at temperatures in the range of 0° C. to 100° C.

When this step is conducted, a 4-fluorobiphenyl derivative of formula (I-c) can also be obtained instead of the 4-fluorobiphenyl derivative of formula (I-a).

Step 6

In this step, a 4-fluorobiphenyl derivative of formula (I-b) is produced by hydrolyzing the 4-fluorobiphenyl derivative of formula (I-a) obtained in Step 5 by use of a base.

Examples of a base for the hydrolysis employed in this step are hydroxides of alkaline metals and alkaline earth metals such as sodium hydroxide, potassium hydroxide, calcium hydroxide, and barium hydroxide.

In this step, such a base is used in an amount in the range of 1 to 3 equivalents, preferably in the range of 1 to 2 equivalents, to one mole of the 4-fluorobiphenyl derivative of formula (I-a).

The reaction is usually carried out in water, or in a mixed solvent of water and a solvent which is miscible water, such as methanol and ethanol, at temperatures in the range of 0° to 80° C.

The 4-fluorobiphenyl derivative of formula (I-b) can be obtained in the form of an alkaline metal salt or alkaline earth metal salt thereof by use of one equivalent of a base for use in the hydrolysis. With the hydrolysis reaction and neutralization, the 4-fluorobiphenyl derivative of formula (I-b) can be obtained.

Step 7

In this step, a 4-fluorobiphenyl derivative of formula (I-c) is produced by subjecting the 4-fluorobiphenyl derivative of formula (I-b) in which $R^4$ is a hydrogen atom, which is obtained in Step 6, to ring closure by the application of heat.

The reaction in this step is carried out in a neutral or acidic condition, in an inert solvent, for example, an aromatic hydrocarbon such as toluene, and xylene, a halogenated hydrocarbon such as dichloromethane, chloroform, and 1,2-dichloroethane; an ester such as methyl acetate; or in a mixed solvent of any of the above solvents.

The reaction can be carried out at temperatures in the range of room temperature to 150° C.

When the above reaction is carried out in an acidic condition, acids such as trifluoroacetic acid, and p-toluenesulfonic acid can be employed.

Furthermore, this step can be conducted by use of a condensing agent, for example, carbodiimide reagents such as dicyclohexylcarbodiimide (DCC).

Furthermore, the 4-fluorobiphenyl derivative of formula (I) can be produced by conducting the reaction in the same manner as in the previously mentioned reaction scheme 1 from a cyano derivative of the following formula (IX), in which the benzyl group in the cyano derivative of formula (IV) is replaced by a lower alkyl group, an alkoxyalkyl group, or a hydroxyalkyl group.

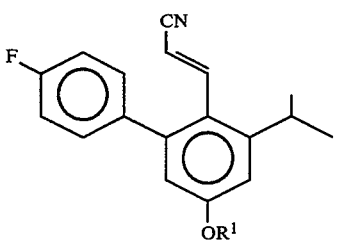

wherein R¹ is the same as defined previously.

When the reaction is conducted in accordance with the previously mentioned reaction scheme 1 by using the cyano derivative of formula (VI), the previously mentioned Step 4 and Step 5 can be omitted.

The features of this invention will become apparent in the course of the following description of exemplary embodiments which are given for illustration of the invention and are not intended to be limiting thereof.

REFERENCE EXAMPLE 1

(E)-3-[5-benzyloxy-4'-fluoro-3-(propan-2-yl)biphenyl-2-yl]-2-propenal

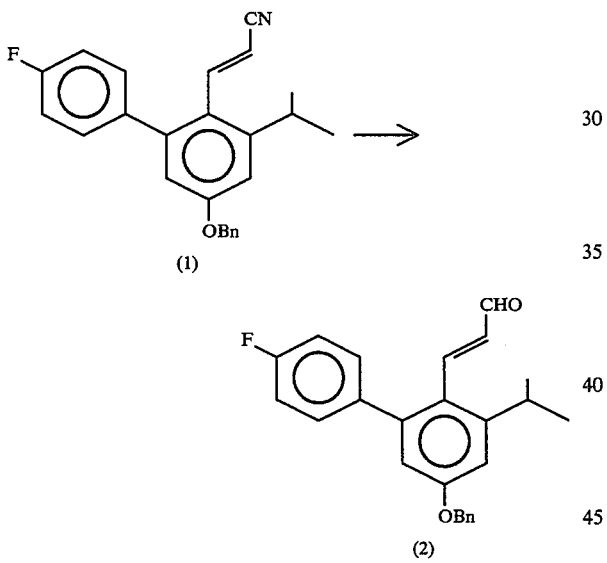

3.18 g (8.57 mmol) of (E)-3-[5-benzyloxy-4'-fluoro-3-(propan-2-yl)biphenyl-2-yl]-2-propenenitrile (Compound 1) was dissolved in 20 ml of anhydrous toluene. To this solution, 10 ml (17.6 mmol) of 25% hexane solution of diisobutylaluminum hydride was added in a stream of argon at −78° C., and the mixture was stirred for 50 minutes.

To this reaction mixture, methanol was added until bubbles were not formed any longer in the reaction mixture.

The reaction mixture was then added to a 1N hydrochloric acid. With the addition of ethyl acetate thereto, the mixture was stirred for 1 hour.

The ethyl acetate layer of the mixture was separated and successively was washed with water, a saturated aqueous solution of sodium hydrogencarbonate, and then with a saturated aqueous solution of sodium chloride, and dried over magnesium sulfate and then concentrated.

The residue was chromatographed on silica gel and eluted with a mixed solvent of dichloromethane and hexane (2:1 to 3:1), whereby (E)-3-[5-benzyloxy-4'-fluoro-3-(propan-2-yl)biphenyl-2-yl]-2-propenal (Compound 2) was obtained in a yield of 3.02 g (94.2%).

Melting point: 93.0°–93.2° C. (colorless fine particle-shaped crystals, recrystallized from a mixed solvent of ethyl acetate and hexane)

¹HMNR (300 MHz, CDCl₃)

δ 1.27(d, J=6.7 Hz, 6H), 3.30(hept, J=6.7 Hz, 1H), 5.10(s, 2H), 5.95 (dd, J=16.2 and 7.8 Hz, 1H), 6.78(d, J=2.6 Hz, 1H), 7.01(d, J=2.6 Hz, 1H), 7.02–7.12(m, 2H), 7.16–7.28(m, 2H), 7.30–7.50(m, 5H), 7.49(d, J=16.2 Hz, 1H), 9.47(d, J=7.8 Hz, 1H) ppm.

IR (KBr): 2968, 1676, 1596, 1512cm⁻¹.

Mass (m/z, %): 374M⁺, 10), 331(84), 183(6), 91(100).

REFERENCE EXAMPLE 2

Ethyl (E)-7-[5-benzyloxy-4'-fluoro-3-(propan-2-yl)biphenyl-2-yl]-5-hydroxy-3-oxo-6-heptenoate

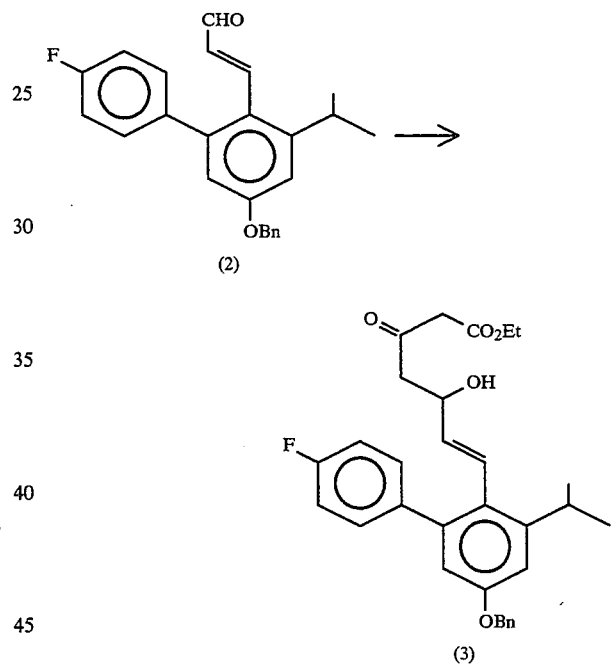

In a stream of argon, 322 mg (8.05 mmol) of a 60% sodium hydride was suspended in 10.0 ml of anhydrous THF, and then 1.0 ml (8.05 mmol) of ethyl acetoacetate was added to the suspension. This reaction mixture was stirred for 30 minutes.

To this reaction mixture, 5.0 ml (7.86 mmol) of a 15% hexane solution of butyllithium was added, and the mixture was stirred for 20 minutes, and was then cooled to −78° C.

A solution of 2.26 g (6.05 mmol) of Compound 2 synthesized in Reference Example 1 in 20 ml of anhydrous THF was added dropwise to the above reaction mixture, and this reaction mixture was stirred for 2 hours and 20 minutes.

The reaction mixture was added to 1N hydrochoric acid, and the mixture was then extracted with ethyl acetate. The extract layer was successively washed with a saturated aqueous solution of sodium chloride, a saturated aqueous solution of sodium hydrogencarbonate, and then with a saturated aqueous solution of sodium chloride three times, dried over magnesium sulfate, and concentrated.

The residue was chromatographed on silica gel and eluted with a mixed solvent of ethyl acetate and hexane (1:4 to 1:3), whereby ethyl (E)-7-[5-benzyloxy-4'-fluoro-3-(propan-2-yl)biphenyl-2-yl]-5-hydroxy-3-oxo-6-heptenoate (Compound 3) was obtained in a yield of 2.13 g (70.0%).

Melting point: 83.5°-84.0° C. (colorless, fine particle-shaped crystals, recrystallized from a mixed solvent of ethyl acetate and hexane)

$^1$HNMR (300 MHz, CDCl$_3$)

δ 1.21(d, J=6.8 Hz, 3H), 1.21(d, J=6.8 Hz, 3H), 1.28(t, J=7.2 Hz, 3H), 2.40-2.58(m, 3H), 3.21(hept, J=6.8 Hz, 1H), 3.41(s, 2H), 4.20(q, J=7.2 Hz, 2H), 4.48-4.60(m, 1H), 5.06(s, 2H), 5.18(dd, J=16.1 and 6.2 Hz, 1H), 6.55(dd, J=16.1 and 1.3 Hz, 1H), 6.74(d, J=2.6 Hz, 1H), 6.94(d, J=2.6 Hz, 1H), 6.98-7.10(m, 2H), 7.16-7.32(m, 2H), 7.28-7.50(m, 5H) ppm.

IR (KBr): 3448, 2968, 1726, 1706, 1602, 1512 cm$^{-1}$.

Mass (m/z, %): 504(M$^+$, trace), 331 (100), 91 (93), 43 (14).

REFERENCE EXAMPLE 3

Ethyl (E)-7-[5-benzyloxy-4'-fluoro-3-(propan-2-yl)biphenyl-2-yl]-3,5-dihydroxy-6-heptenoate

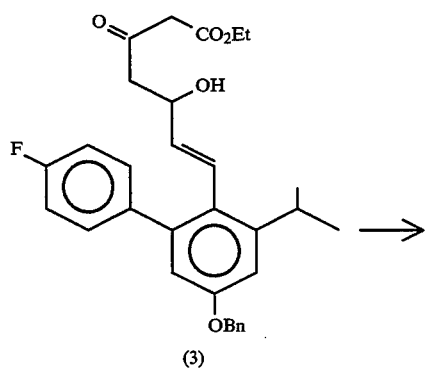

(3)

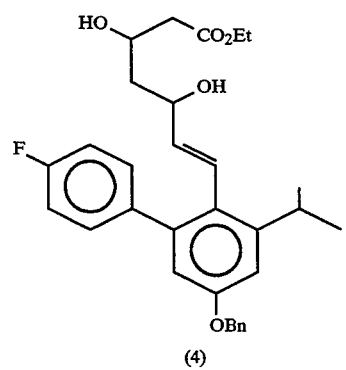

(4)

6.50 ml (6.50 mmol) of a 1.0M THF solution of triethylborane was added to 25 mg (0.248 mmol) of pivalic acid, and the mixture was stirred at room temperature in an atmosphere of argon for 1 hour.

To this mixture, a solution of 2.37 g (4.70 mmol) of Compound 3 synthesized in Reference Example 2 in 20 ml of anhydrous THF was added, and the mixture was stirred for 1 hour.

The reaction mixture was then cooled to −78° C., and 12 ml of methanol was added thereto. To this reaction mixture, 267 mg (7.06 mmol) of sodium borohydride was added, and the mixture was then stirred for 1 hour and 55 minutes.

The reaction mixture was then gradually added to 30 ml of a 30% aqueous solution of hydrogen peroxide which was cooled to 0° C. The mixture was stirred at room temperature overnight. The reaction mixture was then added to a 1N solution of hydrochloric acid. The mixture was then extracted with ethyl acetate.

The extract layer was successively washed with a saturated aqueous solution of sodium chloride, a saturated aqueous solution of sodium thiosulfate, and then with a saturated aqueous solution of sodium chloride three times, dried over magnesium sulfate, and concentrated.

The residue was chromatographed on silica gel and eluted with a mixed solvent of ethyl acetate and hexane (1:2), whereby ethyl (E)-7-[5-benzyloxy-4'-fluoro-3-(propan-2-yl)biphenyl-2-yl]-3,5-dihydroxy-6-heptenoate (Compound 4) was obtained in the form of a colorless amorphous solid in a yield of 2.03 g (85.3 %).

$^1$HNMR (300 MHz, CDCl$_3$)

δ1.18-1.34(m, 1H), 1.21(d, J=6.8 Hz, 3H), 1.22(d, J=6.8 Hz, 3H), 1.28(t, J=7.2 Hz, 3H), 1.39-1.53(m, 1H), 2.34-2.50(m, 2H), 2.86(d, J=1.7 Hz, 1H), 3.24(hept, J=6.8 Hz, 1H), 3.61(d, J=2.4 Hz, 1H), 4.04-4.18(m, 1H), 4.18(q, J=7.2 Hz, 2H), 4.28-4.40 (m, 1H), 5.06(s, 2H), 5.20(dd, J=16.0 and 6.3 Hz, 1H), 6.52(dd, J=16.0 and 1.0 Hz, 1H), 6.74(d, J=2.6 Hz, 1H), 6.94(d, J=2.6 Hz, 1H), 6.96-7.08(m, 2H), 7.18-7.26(m, 2H), 7.28-7.50(m, 5H)ppm.

IR (KBr): 3420, 2956, 1718, 1598, 1514 cm$^{-1}$.

Mass (m/z, %): 506 (M$^+$, 5), 442 (34), 357 (7), 344 (7), 91 (100).

REFERENCE EXAMPLE 4

Ethyl (E)-7-[4'-fluoro-5-hydroxy-3-(propan-2-yl)biphenyl-2-yl]-3,5-dihydroxy-6-heptenoate:

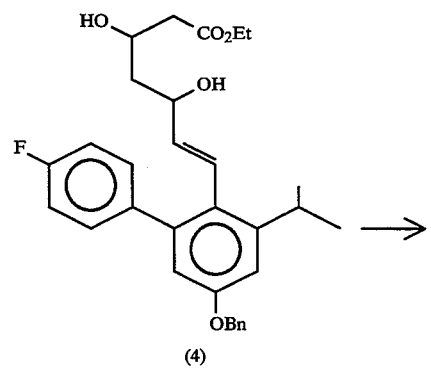

(4)

-continued

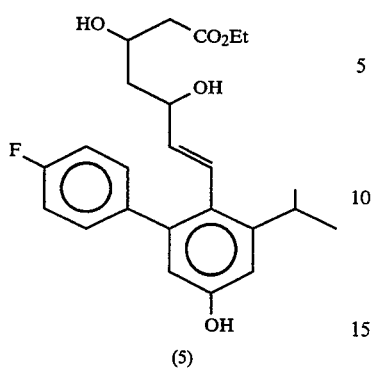

450 mg (0.889 mmol) of Compound 4 synthesized in Reference Example 3 was dissolved in 3.0 ml of methanol in an atmosphere of argon. To this solution, 1.2 ml (8.91 mmol) of triethylamine and 45 mg of 10% Pd-C were added. To this mixture, a solution of 0.3 ml (7.95 mmol) of formic acid in 2.0 ml of methanol was added. This reaction mixture was stirred at room temperature for 6 hours and 25 minutes. With the addition of ethyl acetate, this reaction mixture was filtered through Celite. The filtrate was added to a saturated aqueous solution of sodium chloride. The mixture was then extracted with ethyl acetate.

The extract layer was washed with a saturated aqueous solution of sodium chloride two times, dried over magnesium sulfate, and concentrated.

The residue was chromatographed on silica gel and eluted with a mixed solvent of ethyl acetate and hexane (1:1), whereby ethyl (E)-7-[4'-fluoro-5-hydroxy-3-(propan-2-yl)biphenyl-2-yl]-3,5-dihydroxy-6-heptenoate (Compound 5) was obtained in the form of a colorless oil in a yield of 326 mg (88.1%).

¹HNMR (300 MHz, CDCl₃)

δ 1.17–1.34(m, 1H), 1.21(d, J=6.8 Hz, 3H), 1.22(d, J=6.8 Hz, 3H), 1.28(t, J=7.1 Hz, 3H), 1.39–1.51(m, 1H), 2.38–2.44(m, 2H), 2.84–2.90(m, 1H), 3.22(hept, J=6.8 Hz, 1H), 3.58–3.64(s with fine coupling, 1H), 4.04–4.16(m, 1H), 4.18(q, J=7.1 Hz, 2H), 4.28–4.39(m, 1H), 4.83(s, 1H), 5.19(dd, J=16.0 and 6.4 Hz, 1H), 6.50(dd, J=16.0 and 1.1 Hz, 1H), 6.59(d, J=2.6 Hz, 1H), 6.78(d, J=2.6 Hz, 1H), 6.94–7.10(m, 2H), 7.14–7.26(m, 2H)ppm.

IR (liquid film): 3444, 2968, 1894, 1716, 1606, 1582, 1512 cm⁻¹.

Mass (m/z, %): 416 (M⁺, 49), 398 (38), 283 (37), 267 (45), 242 (100), 230 (71), 213 (56), 201 (76), 183 (26), 143 (21).

EXAMPLE 1

Ethyl (E)-7-[4'-fluoro-3-(propan- 2-yl) -5-[2-(2-tetrahydropyranyloxy)ethyl]biphenyl -2-yl ]-3,5-dihydroxy-6-heptenoate

95 mg (0.228 mmol) of Compound 5 synthesized in Reference Example 4 was dissolved in 0.05 ml of anhydrous DMF in an atmosphere of argon. To this solution, 158 mg (1.14 mmol ) of potassium carbonate and a solution of 292 mg (1.141 mmol) of 1-iodo-2-(2-tetrahydropyranyloxy)ethane in 0.5 ml of anhydrous DMF were added. This reaction mixture was stirred at room temperature for 7 hours.

The reaction mixture was then added to a saturated aqueous solution of sodium chloride, and the mixture was extracted with ethyl acetate.

The extract layer was successively washed with a saturated aqueous solution of ammonium chloride, and then with a saturated aqueous solution of sodium chloride three times, dried over magnesium sulfate, and concentrated.

The residue was chromatographed on silica gel and eluted with a mixed solvent of ethyl acetate and hexane (2:3 to 1:1), whereby ethyl (E)-7-[4'-fluoro-3-(propan-2-yl)-5-[2-(2-tetrahydropyranyloxy)ethyl]-biphenyl-2-yl]-3,5-dihydroxy-6-heptenoate (Compound 6) was obtained in the form of a colorless oil in a yield of 40 mg (32.9%).

¹HNMR (300 MHz, CDCl₃)

δ1.18–1.34(m, 1H), 1.21(d, J=6.8 Hz, 3H), 1.22(d, J=6.8 Hz, 3H), 1.28(t, J=7.1 Hz, 3H), 1.36–1.90(m, 7H), 2.33–2.50(m, 2H), 2.89(d, J=2.1 Hz, 1H), 3.23(hept, J=6.8 Hz, 1H), 3.46–3.60(m, 1H), 3.63(d, J=2.2 Hz, 1H), 3.76–3.96(m, 2H), 3.98–4.24(m, 4H), 4.18(q, J=7.1 Hz, 2H), 4.28–4.39(m, 1H), 4.68–4.74(m, 1H), 5.19(dd, J=16.0 and 6.4 Hz, 1H), 6.51(dd, J=16.0 and 0.9 Hz, 1H), 6.68(d, J=2.6 Hz, 1H), 6.90(d, J=2.6 Hz, 1H), 6.96–7.08(m, 2H), 7.16–7.28(m, 2H)ppm.

IR (liquid film): 3448, 2944, 1728, 1604, 1514 cm$^{-1}$.

Mass (m/z, %): 544(M$^+$, 22), 480 (35), 267 (18), 241 (22), 230 (8), 183 (11), 85 (100), 73 (27).

EXAMPLE 2

Ethyl (E)-7-[4'-fluoro-5-(2-hydroxyethoxy)-3-(propan-2-yl)biphenyl-2-yl]-3,5-dihydroxy-6-heptenoate:

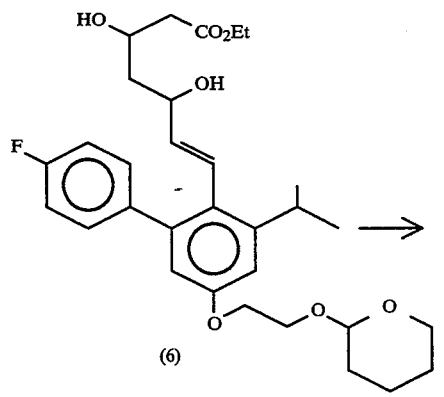

(6)

→

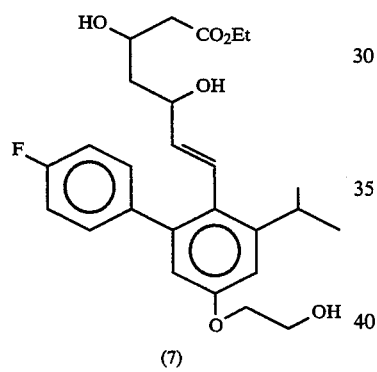

(7)

10 mg (0.018 mmol) of Compound 6 synthesized in Example 1 was dissolved in 0.3 ml of methanol. To this solution, 1 mg (0.004 mmol) of pyridinium p-toluenesulfonate was added. This mixture was stirred at room temperature for 7 hours.

This reaction mixture was then added to a saturated aqueous solution of sodium chloride, and the mixture was extracted with ethyl acetate.

The extract layer was washed with a saturated aqueous solution of sodium chloride, dried over magnesium sulfate, and concentrated.

The residue was chromatographed on silica gel and eluted with a mixed solvent of ethyl acetate and hexane (2:3 to 1:1 to 3:2), whereby ethyl (E)-7-[4'-fluoro-5-(2-hydroxyethoxy)-3-(propan-2-yl)biphenyl-2-yl]-3,5-dihydroxy-6-heptenoate (Compound 7) was obtained in the form of a colorless oil in a yield of 4 mg (47.3%).

$^1$HNMR (300 MHz, CDCl$_3$)

δ 1.18–1.34(m, 1H), 1.22(d, J=6.8 Hz, 3H), 1.23(d, J=6.8 Hz, 3H), 1.28(t, J=7.2 Hz, 3H), 1.38–1.54(m, 1H), 2.02(t, J=6.2 Hz, 1H), 2.34–2.50(m, 2H), 2.89(d, J=2.0 Hz, 1H), 3.25(hept, J=6.8 Hz, 1H), 3.62(d, J=2.0 Hz, 1H), 3.92–4.01(m, 2H), 4.05–4.16(m, 3H), 4.18(q, J=7.2 Hz, 2H), 4.28–4.39(m, 1H), 5.20(dd, J=16.1 and 6.3 Hz, 1H), 6.51(dd, J=16.1 and 1.2 Hz, 1H), 6.66(d, J=2.6 Hz, 1H), 6.88(d, J=2.6 Hz, 1H), 6.96–7.08(m, 2H), 7.16–7.28(m, 2H)ppm.

IR (liquid film): 3420, 2968, 1734, 1602, 1512 cm$^{-1}$.

Mass (m/z, %): 460 (M$^+$, 34), 396 (100), 311 (66), 298 (58), 285 (74), 267 (25), 257 (45), 241 (46), 213 (51), 201 (21), 199 (28), 183 (27), 143 (11).

EXAMPLE 3

Sodium (E)-7-[4'-fluoro-5-(2-hydroxyethoxy)-3-(propan-2-yl)biphenyl-2-yl]-3,5-dihydroxy-6-heptenoate:

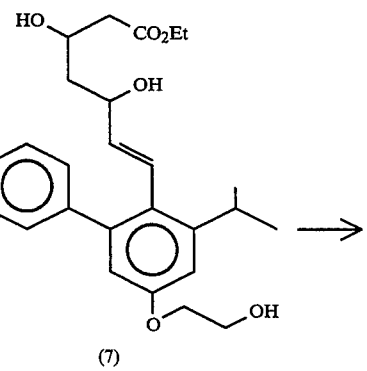

(7)

→

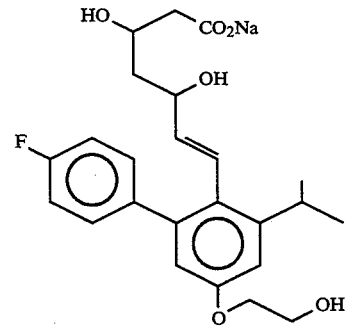

(8)

18 mg (0.039 mmol) of Compound 7 synthesized in Example 2 was dissolved in 0.5 ml of ethanol. To this solution, 0.078 ml (0.039 mmol) of a 0.5N aqueous solution of sodium hydroxide was added, and this reaction mixture was stirred at room temperature in an atmosphere of argon for 40 minutes.

The reaction mixture was concentrated, dissolved in water and subjected to freeze-drying, whereby sodium (E)-7-[4'-fluoro-5-(2-hydroxyethoxy)-3-(propan-2-yl)biphenyl-2-yl]-3,5-dihydroxy-6-heptenoate (Compound 8) was obtained in the form of colorless, amorphous solid in a yield of 15 mg (84.3%).

$^1$HNMR (300 MHz, CD$_3$OD)

δ 1.27(d, J=6.8 Hz, 3H), 1.27(d, J=6.8 Hz, 3H), 1.28–1.44(m, 1H), 1.52–1.68(m, 1H), 2.23(dd, J=15.3 and 7.8 Hz, 1H), 2.33(dd, J=15.3 and 4.5 Hz, 1H), 3.40(hept, J=6.8 Hz, 1H), 3.80–3.98(m, 3H), 4.04–4.14(m, 2H), 4.20–4.34(m,1H), 5.27(dd, J=16.1 and 6.6 Hz, 1H), 6.52(dd, J=16.1 and 1.0 Hz, 1H), 6.70(d, J=2.7 Hz, 1H), 6.94(d, J=2.7Hz, 1H), 7.06–7.20(m, 2H), 7.24–7.36(m, 2H) ppm.

IR (KBr): 3408, 2964, 1602, 1574, 1512 cm$^{-1}$.

Mass (FAB-neg, m/z, %): 453 ([M-H]$^-$, 7), 432 (29), 431 (100), 325 (23).

EXAMPLE 4

Ethyl (E)-7-[4'-fluoro-5-(2-methoxyethoxy)-3-(propan-2-yl)-biphenyl-2-yl]-3,5-dihydroxy-6-heptenoate:

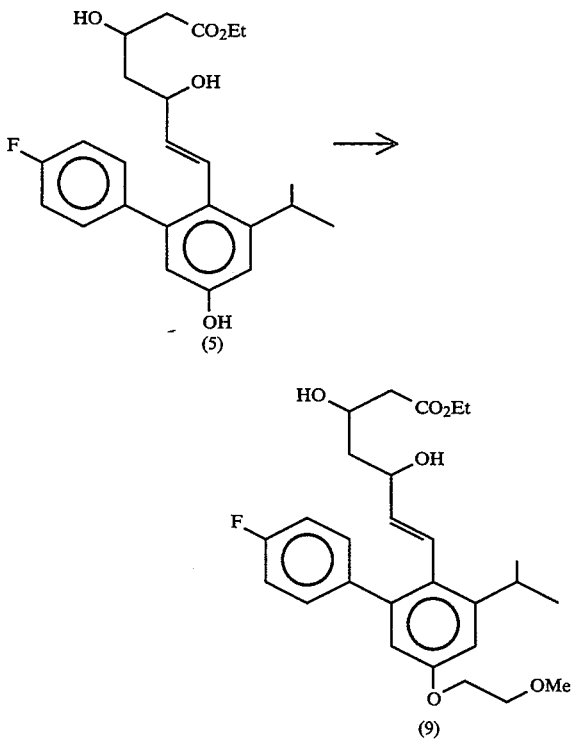

85 mg (0.20 mmol) of Compound 5 synthesized in Reference Example 4 was dissolved in 0.8 ml of anhydrous DMF. To this solution, 115 mg (0.83 mmol) of potassium carbonate and a solution of 125 mg (0.67 mmol) of 1-iodo-2-methoxyethane in 0.4 ml of DMF were added, and this reaction mixture was stirred in a stream of argon at room temperature for 2 hours.

To this reaction mixture, 137 mg (0.99 mmol) of potassium carbonate and a solution of 127 mg (0.68 mmol) of 1-iodo-2-methoxyethane in 0.2 ml of DMF were added, and this reaction mixture was stirred for 3 hours and 10 minutes.

The mixture was added to water, and was then extracted with ethyl acetate. The extract layer was washed with a saturated aqueous solution of sodium chloride, dried over magnesium sulfate, and concentrated.

The residue was chromatographed on silica gel and eluted with a mixed solvent of dichloromethane and ethyl acetate (5:1). The eluent was concentrated, and was then rechromatographed on silica gel and eluted with a mixed solvent of hexane and ethyl acetate (1:1), whereby ethyl (E)-7-[4'-fluoro-5-(2-methoxyethoxy)-3-(propan-2-yl)-biphenyl-2-yl]-3,5-dihydroxy-6-heptenoate (Compound 9) was obtained in the form of a colorless oil in a yield of 26 mg (26.8%).

$^1$HNMR (300 MHz, CDCl$_3$) δ 1.18–1.33(m, 1H), 1.21(d, J=6.8 Hz, 3H), 1.22(d, J=6.8 Hz, 3H), 1.28(t, J=7.2 Hz, 3H), 1.39–1.50(m, 1H), 2.33–2.49(m, 2H), 2.83(s with fine coupling, 1H), 3.23(hept, J=6.8 Hz, 1H), 3.46(s, 3H), 3.61(s with fine coupling, 1H), 3.72–3.79(m, 2H), 4.04–4.22(m, 3H), 4.18(q, J=7.2 Hz, 2H), 4.28–4.39(m, 1H), 5.19(dd, J=16.1 and 6.3 Hz, 1H), 6.51(dd, J=16.1 and 1.2 Hz, 1H), 6.66(d, J=2.6 Hz, 1H), 6.90(d, J=2.6 Hz, 1H), 6.96–7.07(m, 2H), 7.16–7.29(m, 2H)ppm.

IR (liquid film): 3464, 2968, 2932, 1734, 1602cm$^{-1}$.

Mass (m/z, %): 474 (M$^+$, 100), 456 (67), 410 (42), 341 (39), 325 (38), 301 (51), 300 (36), 299 (44), 288 (35), 287 (34), 241 (40), 239 (35), 59 (94).

EXAMPLE 5

Sodium (E)-7-[4'-fluoro-5-(2-methoxyethoxy)-3-(propan-2-yl)biphenyl-2-yl]-3,5-dihydroxy-6-heptenoate:

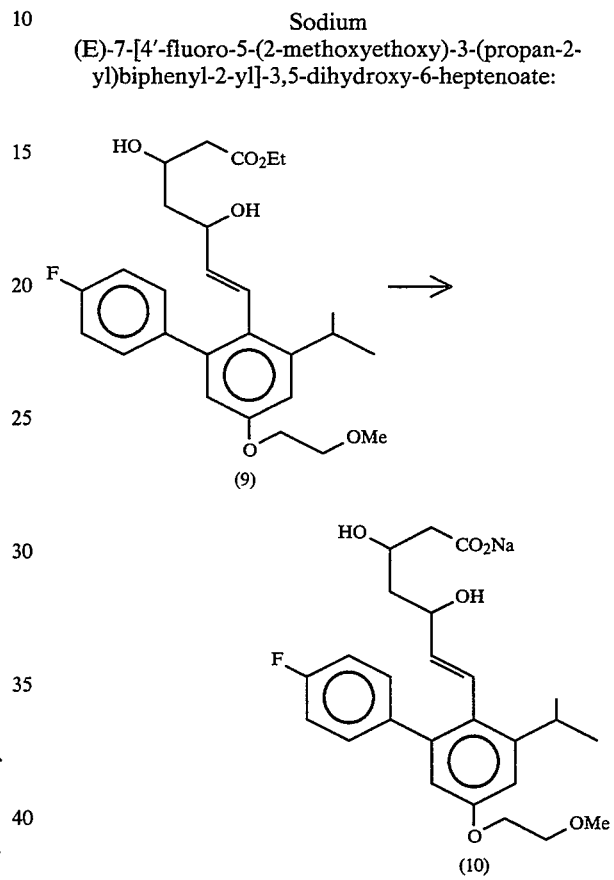

22 mg (0.046 mmol) of Compound 9 synthesized in Example 4 was dissolved in 1.0 ml of ethanol. To this solution, 0.46 ml (0.046 mmol) of a 0.1N aqueous solution of sodium hydroxide was added, and the mixture was stirred in a stream of argon at room temperature for 2 hours.

The reaction mixture was then concentrated, dissolved in an appropriate amount of water and subjected to freeze-drying, whereby sodium (E)-7-[4'-fluoro-5-(2-methoxyethoxy)-3-(propan-2-yl)biphenyl-2-yl]-3,5-dihydroxy-6-heptenoate (Compound 10) was obtained in the form of colorless, amorphous solid in a quantitative yield.

$^1$HNMR (300 MHz, CD$_3$OD)

δ 1.26(d, J=6.8 Hz, 3H), 1.26(d, J=6.8 Hz, 3H), 1.36(ddd, J=13.7, 6.3 and 4.3 Hz, 1H), 1.59(ddd, J=13.7, 8.8 and 7.4 Hz, 1H), 2.22(dd, J=15.4 and 7.8 Hz, 1H), 2.33(dd, J=15.4 and 4.6 Hz, 1H), 3.39(hept, J=6.8 Hz, 1H), 3.46(s, 3H), 3.74–3.81(m, 2H), 3.80–3.91(m, 1H), 4.12–4.19(m, 2H), 4.21–4.31(m, 1H), 5.26(dd, J=16.1 and 6.6 Hz, 1H), 6.51(dd, J=16.1 and 1.0 Hz, 1H), 6.68(d, J=2.6 Hz, 1H), 6.92(d, J=2.6 Hz, 1H), 7.05–7.17(m, 2H), 7.24–7.35(m, 2H)ppm.

IR (KBr): 3448, 2968, 2932, 1602, 1574 cm$^{-1}$,

Mass (FAB-neg, m/z, %): 467([M-H]$^-$, 5), 445 (100).

EXAMPLE 6

Ethyl (E)-7-[4'-fluoro-5-[2-(2-methoxyethoxy)ethoxy]-3-(propan-2-yl)biphenyl-2-yl]-3,5-dihydroxy-6-heptenoate:

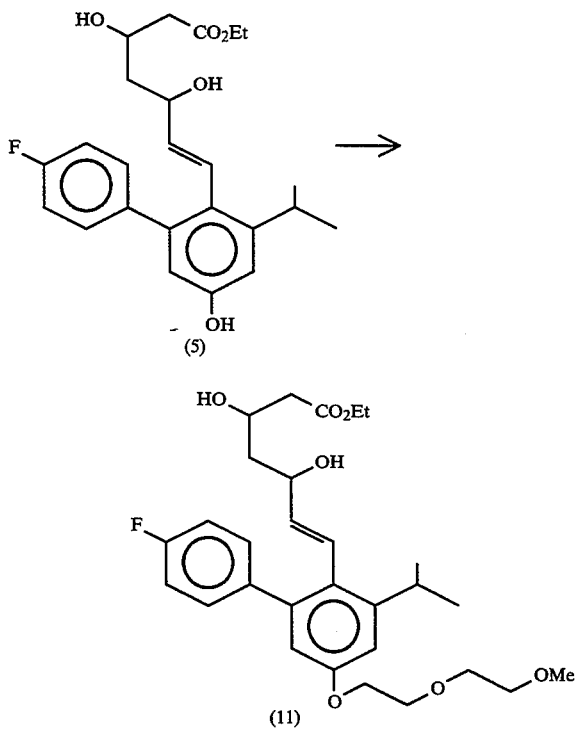

100 mg (0.240 mmol) of Compound 5 synthesized in Reference Example 4 was dissolved in 1.0 ml of anhydrous DMF. To this solution, 166 mg (1.20 mmol) of potassium carbonate and a solution of 276 mg (1.20 mmol) of 1-iodo-2-(2-methoxyethoxy)ethane in 0.5 ml of anhydrous DMF were added. This reaction mixture was stirred at room temperature for 8 hours and 25 minutes.

The reaction mixture was then added to a saturated aqueous solution of sodium chloride. The mixture was then extracted with ethyl acetate. The extract layer was washed with a saturated aqueous solution of sodium chloride two times, dried over magnesium sulfate, and concentrated.

The residue was chromatographed on silica gel and eluted with a mixed solvent of ethyl acetate and hexane (1:1), whereby ethyl (E)-7-[4'-fluoro-5-[2-(2-methoxyethoxy)ethoxy]-3-(propan-2-yl)biphenyl-2-yl]-3,5-dihydroxy-6-heptenoate (Compound 11) was obtained in the form of a colorless oil in a yield of 26 mg (20.9%).

$^1$HNMR (300 MHz, CDCl$_3$)

δ 1.18–1.33(m, 1H), 1.21(d, J=6.8 Hz, 3H), 1.22(d, J=6.8 Hz, 3H), 1.28(t, J=7.1 Hz, 3H), 1.38–1.53(m, 1H), 2.33–2.50(m, 2H), 2.84(d, J=2.0 Hz, 1H), 3.23(hept, J=6.8 Hz, 1H), 3.39(s, 3H), 3.52–3.64(m, 2H), 3.61(d, J=2.3 Hz, 1H), 3.68–3.76(m, 2H), 3.80–3.92(m, 2H), 4.02–4.22(m, 3H), 4.18(q, J=7.1 Hz, 2H), 4.22–4.40(m, 1H), 5.19(dd, J=16.0 and 6.4 Hz, 1H), 6.51(d, J=16.0 Hz, 1H), 6.65(d, J=2.7 Hz, 1H), 6.88(d, J=2.7 Hz, 1H), 6.96–7.06(m, 2H), 7.16–7.24m, 2H)ppm.

IR (liquid film): 3456, 2964, 2932, 1736, 1602, 1512cm$^{-1}$.

Mass (m/z, %): 518 (M$^+$, 52), 500 (32), 454 (93), 369 (32), 267 (32), 241 (36), 239 (43), 230 (15), 183 (20), 103 (57), 59 (100).

EXAMPLE 7

Sodium (E)-7-[4'-fluoro-5-[2-(2-methoxyethoxy)ethoxy]-3-(propan-2-yl)biphenyl-2-yl]-3,5-dihydroxy-6-heptenoate

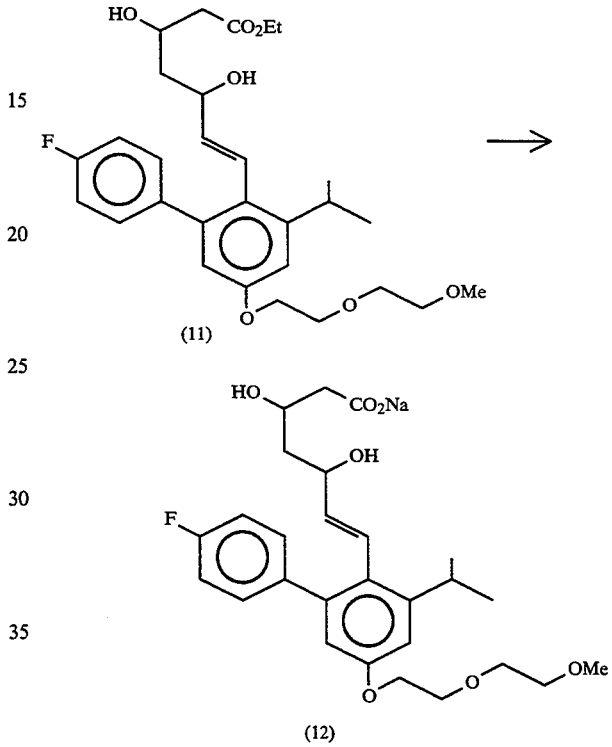

23 mg (0.044 mmol) of Compound 11 synthesized in Example 6 was dissolved in 0.5 ml of ethanol. To this solution, 0.089 ml (0.044 mmol) of a 0.5N aqueous solution of sodium hydroxide was added, and the mixture was stirred in an atmosphere of argon at room temperature for 25 minutes.

The reaction mixture was then concentrated, dissolved in an appropriate amount of water and subjected to freeze-drying, whereby sodium (E)-7-[4'-fluoro-5-[2-(2-methoxyethoxy)ethoxy]-3-(propan-2-yl)biphenyl-2-yl]3,5-dihydroxy-6-heptenoate (Compound 12) was obtained in the form of a colorless, amorphous solid in a yield of 22 mg (94.6%).

$^1$HNMR (300 MHz, CD$_3$OD)

δ 1.27(d, J=6.8 Hz, 6H), 1.28–1.42(m, 1H), 1.52–1.66(m, 1H), 2.23(dd, J=15.3 and 7.9 Hz, 1H), 2.33(dd, J=15.3 and 4.5 Hz, 1H), 3.32–3.46(m, 1H), 3.40(s, 3H), 3.56–3.66(m, 2H), 3.70–3.78(m, 2H), 3.80–3.92(m, 3H), 4.14–4.22(m, 2H), 4.22–4.32(m, 1H), 5.27(dd, J=16.1 and 6.6 Hz, 1H), 6.52(dd, J=16.1 and 0.9 Hz, 1H), 6.69(d, J=2.6 Hz, 1H), 6.92(d, J=2.6 Hz, 1H), 7.06–7.18(m, 2H), 7.24–7.36(m, 2H)ppm.

IR (KBr): 3432, 2964, 2936, 1602, 1572, 1512 cm$^{-1}$.

Mass (FAB-neg, m/z, %): 511 ([M-H]$^-$, 11), 490 (35), 489 (100), 283 (47), 281 (55), 253 (41).

EXAMPLE 8

Ethyl (E)-7-[4'-fluoro-3-(propan-2-yl)-5-(2-pyridylmethyloxy)biphenyl-2-yl]-3,5-dihydroxy-6-heptenoate

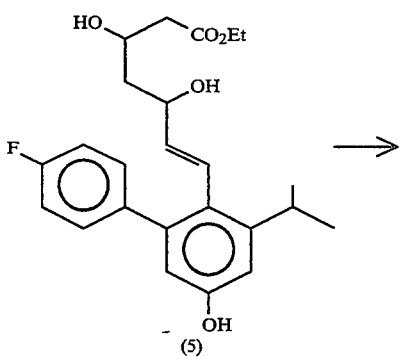

(5)

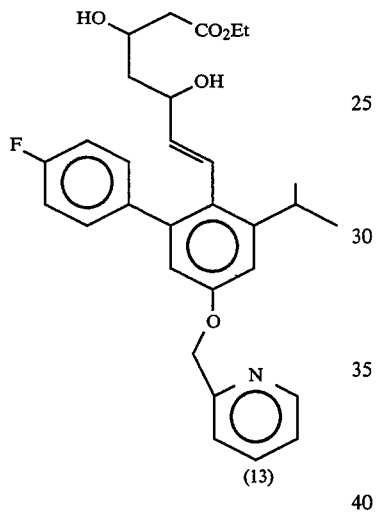

(13)

62 mg (0.15 mmol) of Compound 5 synthesized in Reference Example 4 was dissolved in 1.0 ml of DMF. To this solution, 200 mg (1.45 mmol) of potassium carbonate and 0.15 ml of 2-chloromethylpyridine were added, and this reaction mixture was stirred for 1 hour and 30 minutes.

The reaction mixture was then added to water. The mixture was then extracted with ethyl acetate. The extract layer was washed with a saturated aqueous solution of sodium chloride, dried over magnesium sulfate, and concentrated.

The residue was chromatographed on silica gel and eluted with a mixed solvent of hexane and ethyl acetate (1:1), whereby ethyl (E)-7-[4'-fluoro-3-(propan-2-yl)-5-(2-pyridylmethyloxy)biphenyl-2-yl]-3,5-dihydroxy-6-heptenoate (Compound 13) was obtained in the form of a colorless, amorphous solid in a yield of 31 mg (41.0%).

$^1$HNMR (300 MHz, CDCl$_3$)

δ 1.17–1.33(m, 1H), 1.20(d, J=6.8 Hz, 3H), 1.21(d, J=6.8 Hz, 3H), 1.28(t, J=7.1 Hz, 3H), 1.39–1.53(m, 1H), 2.33–2.49(m, 2H), 2.88(broad s, 1H), 3.24(hept, J=6.8 Hz, 1H), 3.62(broad s, 1H), 4.04–4.16(m, 1H), 4.18(q, J=7.1 Hz, 2H), 4.28–4.38(m, 1H), 5.20(dd, J=16.1 and 6.4 Hz, 1H), 5.22(s, 2H), 6.51(dd, J=16.1and 1.1 Hz, 1H), 6.75(d, J=2.7 Hz, 1H), 6.95(d, J=2.7 Hz, 1H), 6.95–7.07(m, 2H), 7.16–7.30(m, 3H), 7.55(d, J=7.7 Hz, 1H), 7.73(td, J=7.7 Hz and 1.8 Hz, 1H), 8.60(d with fine coupling, J=4.9 Hz, 1H)ppm.

IR (KBr): 3432, 2964, 1724, 1602 cm$^{-1}$.

Mass (m/z, %): 507 (M$^+$, 17), 443 (72), 347 (39), 346 (89), 334 (33), 332 (54), 241 (30), 93 (100), 92 (69).

EXAMPLE 9

Sodium (E)-7-[4'-fluoro-3-(propan-2-yl)-5-(2-pyridylmethyloxy)biphenyl-2-yl]-3,5-dihydroxy-6-heptenoate

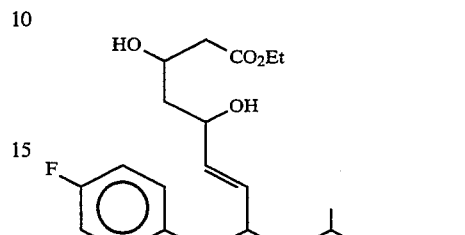

(13)

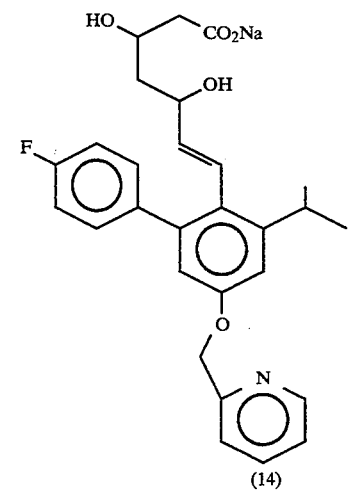

(14)

31 mg (0.061 mmol) of Compound 13 synthesized in Example 8 was dissolved in 1.0 ml of ethanol. To this solution, 0.61 ml (0.061 mmol) of a 0.1N aqueous solution of sodium hydroxide was added, and the mixture was stirred in a stream of argon at room temperature for 1 hour.

The reaction mixture was then concentrated, dissolved in an appropriate amount of water and subjected to freeze-drying, whereby sodium (E)-7-[4'-fluoro-3-(propan-2-yl)-5-(2-pyridylmethyloxy)biphenyl-2-yl]-3,5-dihydroxy-6-heptenoate (Compound 14) was obtained in the form of a colorless, amorphous solid in a quantitative yield.

$^1$HNMR (300 MHz, CD$^3$OD)

δ 1.24 (d, J=6.8 Hz, 6H), 1.36(ddd, J=13.8, 6.3 and 4.4 Hz, 1H), 1.59(ddd, J=13.8, 8.5 and 7.7 Hz, 1H), 2.22(dd, J=15.3 and 7.8 Hz, 1H), 2.33(dd, J=15.3 and 4.5 Hz, 1H), 3.39(hept, J=6.8 Hz, 1H), 3.80–3.93(m, 1H), 4.20–4.33(m, 1H), 5.24(s, 2H), 5.27(dd, J=16.2 and 6.6 Hz, 1H), 6.51(d with fine coupling, J=16.2 Hz, 1H), 6.75(d, J=2.6 Hz, 1H), 6.97(d, J=2.6 Hz, 1H), 7.06–7.18(m, 2H), 7.22–7.34(m, 2H), 7.36–7.46(m, 1H), 7.66(d, J=7.8 Hz, 1H), 7.92(td, J=7.8 Hz and 1.6 Hz, 1H), 8.58(d, J=4.5 Hz, 1H)ppm.

IR (KBr): 3412, 2964, 1602, 1574 cm$^{-1}$.

Mass (FAB-neg, m/z, %): 500([M-H]$^-$, 3), 478 (100), 283 (35), 281 (20).

EXAMPLE 10

Ethyl (E)-7-[4'-fluoro-3-(propan-2-yl)-5-(3-pyridylmethyloxy)biphenyl-2-yl]-3,5-dihydroxy-6-heptenoate

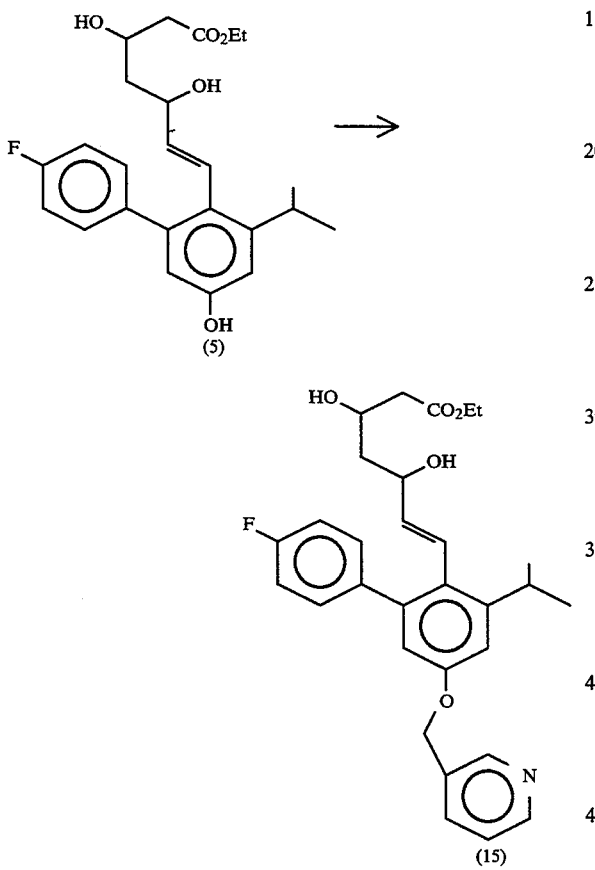

63 mg (0.15 mmol) of Compound 5 synthesized in Reference Example 4 was dissolved in 1.0 ml of DMF. To this solution, 200 mg (1.45 mmol) of potassium carbonate and 0.15 ml of 3-chloromethylpyridine were added. This reaction mixture was stirred in a stream of argon at room temperature for 1 hour and 50 minutes.

The reaction mixture was then added to water. The mixture was then extracted with ethyl acetate. The extract layer was washed with a saturated aqueous solution of sodium chloride, dried over magnesium sulfate, and concentrated.

The residue was chromatographed on silica gel and eluted with a mixed solvent of hexane and ethyl acetate (1:1), whereby ethyl (E)-7-[4'-fluoro-3-(propan-2-yl)-5-(3-pyridylmethyloxy)biphenyl-2-yl]-3,5-dihydroxy-6-heptenoate (Compound 15) was obtained in the form of a colorless, amorphous solid in a yield of 21 mg (27.4%).

$^1$HNMR (300 MHz, CDCl$_3$)

δ 1.19–1.33(m, 1H), 1.22(d, J=6.8 Hz, 3H), 1.23(d, J=6.8 Hz, 3H), 1.28(t, J=7.2 Hz, 3H), 1.39–1.53(m, 1H), 2.34–2.50(m, 2H), 2.93(broad s, 1H), 3.25(hept, J=6.8 Hz, 1H), 3.63(broad s, 1H), 4.04–4.16(m, 1H), 4.18(q, J=7.2 Hz, 2H), 4.28–4.41(m, 1H), 5.09(s, 2H), 5.21(dd, J=16.1 and 6.3 Hz, 1H), 6.52(dd, J=16.1 and 1.1 Hz, 1H), 6.73(d, J=2.7 Hz, 1H), 6.93(d, J=2.7 Hz, 1H), 6.98–7.07(m, 2H), 7.17–7.29(m, 2H), 7.34(ddd, J=7.8, 4.9 and 0.7 Hz, 1H), 7.80(d with fine coupling, J=7.8 Hz, 1H), 8.59(dd, J=4.9 and 1.6 Hz, 1H), 8.69(d, J=1.6 Hz, 1H)ppm.

IR (KBr): 3404, 2968, 1734, 1602 cm$^{-1}$.

Mass (m/z, %): 507 (M$^+$, 8), 443 (49), 415 (22), 376 (24), 346 (61), 241 (49), 92 (100).

EXAMPLE 11

Sodium (E)-7-[4'-fluoro-3-(propan-2-yl)-5-(3-pyridylmethyloxy)biphenyl-2-yl]-3,5-dihydroxy-6-heptenoate

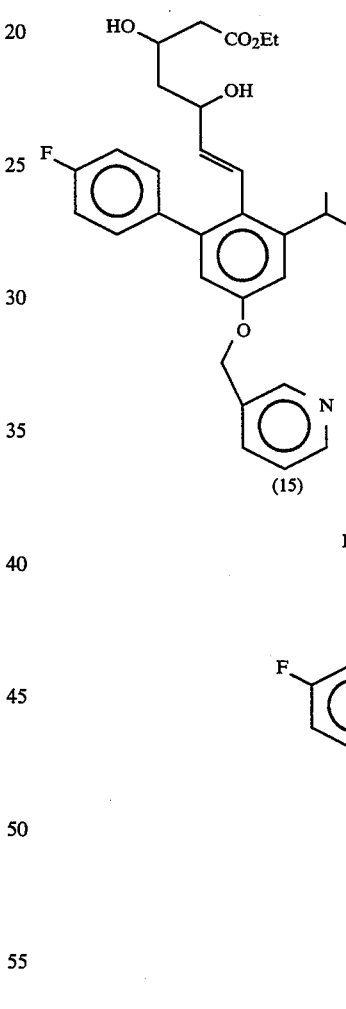

3.25 g (6.41 mmol) of Compound 15 synthesized in Example 10 was dissolved in 30 ml of ethanol. To this solution, 12.82 ml (6.41 mmol) of a 0.5N aqueous solution of sodium hydroxide was added, and the mixture was stirred in a stream of argon at room temperature for 50 minutes.

The reaction mixture was then concentrated, dissolved in an appropriate amount of water and subjected to freeze-drying, whereby sodium (E)-7-[4'-fluoro-3-(propan-2-yl)-5-(3-pyridylmethyloxy)biphenyl-2-yl]-

3,5-dihydroxy-6-heptenoate (Compound 16) was obtained in the form of a colorless, amorphous solid in a quantitative yield.

$^1$HNMR (300 MHz, CD$_3$OD)

δ 1.26(d, J=6.8 Hz, 6H), 1.37(ddd, J=13.7, 6.2 and 4.3 Hz, 1H), 1.60(ddd, J=13.7, 8.7 and 7.5 Hz, 1H), 2.23(dd, J=15.4 and 7.8 Hz, 1H), 2.33(dd, J=15.4 and 4.5 Hz, 1H), 3.40(hept, J=6.8 Hz, 1H), 3.81–3.92(m, 1H), 4.21–4.33(m, 1H), 5.22(s, 2H), 5.28(dd, J=16.1 and 6.5 Hz, 1H), 6.52(dd, J=16.1 and 1.1 Hz, 1H), 6.78(d, J=2.7 Hz, 1H), 6.99(d, J=2.7 Hz, 1H), 7.06–7.18(m, 2H), 7.25–7.35(m, 2H), 7.51(ddd, J=7.9, 4.9 and 0.7 Hz, 1H), 8.00(d with fine coupling, J=7.9 Hz, 1H), 8.54(dd, J=4.9 Hz and 1.6 Hz, 1H), 8.69(d, J=1.4 Hz, 1H)ppm.

IR (KBr): 3384, 2964, 1602, 1578 cm$^{-1}$.

Mass (FAB-neg, m/z, %): 500 ([M-H]$^-$, 4), 478 (100), 283 (82), 281 (50), 255 (37), 253 (38).

EXAMPLE 12

Ethyl (E)-7-[4'-fluoro-3-(propan-2-yl)-5-(4-pyridylmethyloxy)biphenyl-2-yl]-3,5-dihydroxy-6-heptenoate

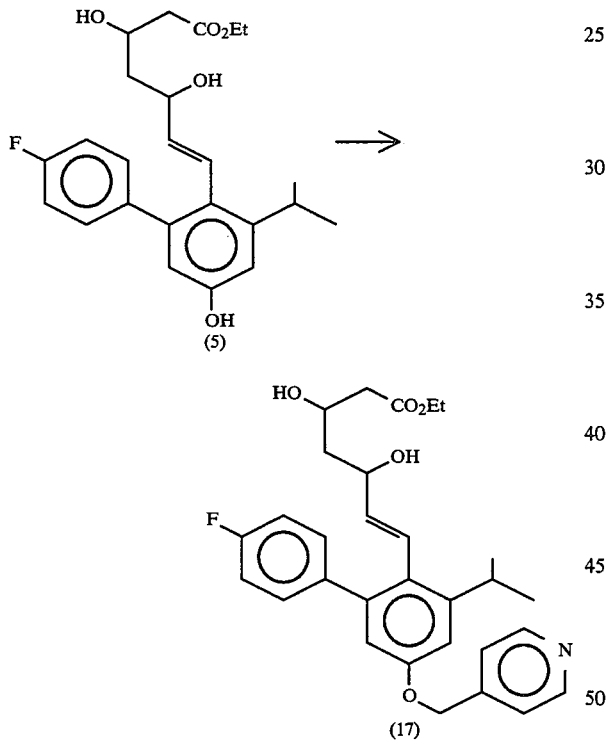

60 mg (0.144 mmol) of Compound 5 synthesized in Reference Example 4 was dissolved in 1.0 ml of anhydrous DMF in an atmosphere of argon. To this solution, 200 mg (1.45 mmol) of potassium carbonate and 0.15 ml of 4-chloromethylpyridine were added. This reaction mixture was stirred at room temperature for 2 hours and 30 minutes.

The reaction mixture was then added to a saturated aqueous solution of sodium chloride. The mixture was then extracted with ethyl acetate. The extract layer was washed with a saturated aqueous solution of sodium chloride three times, dried over magnesium sulfate, and concentrated.

The residue was chromatographed on silica gel and eluted with a mixed solvent of ethyl acetate and hexane (1:3 to 1:2 to 1:1), whereby ethyl (E)-7-[4'-fluoro-3-(propan-2-yl)-5-(4-pyridylmethyloxy)biphenyl-2-yl]-3,5-dihydroxy-6-heptenoate (Compound 17) was obtained in the form of a colorless, amorphous solid in a yield of 40 mg (54.7%).

$^1$HNMR (300 MHz, CDCl$_3$)

δ 1.18–1.36(m, 1H), 1.21(d, J=6.8 Hz, 3H), 1.22(d, J=6.8 Hz, 3H), 1.28(t, J=7.1 Hz, 3H), 1.38–1.53(m, 1H), 2.32–2.52(m, 2H), 3.03(broad s, 1H), 3.25(hept, J=6.8 Hz, 1H), 3.68(broad s, 1H), 4.04–4.20(m, 1H), 4.18(q, J=7.1 Hz, 2H), 4.28–4.40(m, 1H), 5.10(s, 2H), 5.21(dd, J=16.1 and 6.3 Hz, 1H), 6.51(dd, J=16.1 and 1.1 Hz, 1H), 6.70(d, J=2.7 Hz, 1H), 6.92(d, J=2.7 Hz, 1H), 6.96–7.08(m, 2H), 7.16–7.26(m, 3H), 7.37(d, J=6.0 Hz, 2H), 8.62(d with fine coupling, J=6.0 Hz, 2H)ppm.

IR (KBr): 3464, 3160, 2964, 1734, 1602, 1512 cm$^{-1}$.

Mass (m/z, %): 507 (M$^+$, 28), 443 (61), 376 (27), 358 (24), 346 (37), 332 (28), 241 (29), 213 (13), 183 (12), 93 (100), 65 (8).

EXAMPLE 13

Sodium (E)-7-[4'-fluoro-3-(propan-2-yl)-5-(4-pyridylmethyloxy)biphenyl-2-yl]-3,5-dihydroxy-6-heptenoate:

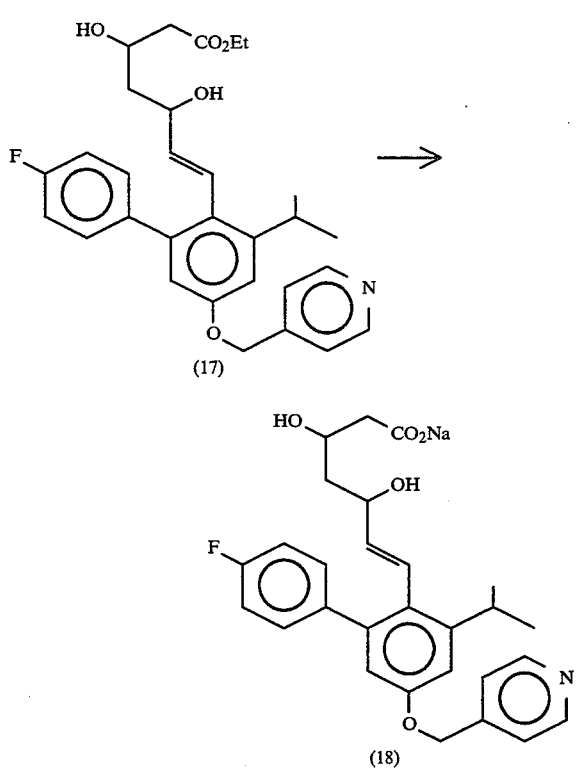

30 mg (0.059 mmol) of Compound 17 synthesized in Example 12 was dissolved in 0.5 ml of ethanol. To this solution, 0.059 ml (0.059 mmol) of a 1N aqueous solution of sodium hydroxide was added, and the mixture was stirred in an atmosphere of argon at room temperature for 55 minutes.

The reaction mixture was then concentrated, dissolved in an appropriate amount of water and subjected to freeze-drying, whereby sodium (E)-7-[4'-fluoro-3-(propan-2-yl)-5-(4-pyridylmethyloxy)biphenyl-2-yl]-3,5-dihydroxy-6-heptenoate (Compound 18) was obtained in the form of a colorless, amorphous solid in yield of 28 mg (94.6%).

¹HNMR (300 MHz, CD₃OD)

δ 1.26(d, J=6.8 Hz, 6H), 1.31–1.43(m, 1H), 1.53–1.67(m, 1H), 2.22(dd, J=15.4 and 7.8 Hz, 1H), 2.33(dd, J=15.4 and 4.6 Hz, 1H), 3.40(hept, J=6.8 Hz, 1H), 3.78–3.93(m, 1H), 4.20–4.33(m, 1H), 5.25(s, 2H), 5.28(dd, J=16.1 and 6.5 Hz, 1H), 6.52(dd, J=16.1 and 0.9 Hz, 1H), 6.76(d, J=2.6 Hz, 1H), 6.98(d, J=2.6 Hz, 1H), 7.07–7.18(m, 2H), 7.25–7.34(m, 2H), 7.58(d, J=6.1 Hz, 2H), 8.57(d with fine coupling, J=6.1 Hz, 2H)ppm.

IR (KBr): 3380, 2964, 1602, 1512 cm⁻¹.

Mass (FAB-neg, m/z, %): 500 ([M-H]⁻, 6), 478 (100), 283 (47), 281 (55), 253 (41).

TEST 1

Determination of Inhibitory Activity on HMG-CoA Reductase

The inhibitory effect on HMG-CoA Reductase of each of representative examples of the 4-fluorobiphenyl derivatives prepared in the above-discussed examples was determined in accordance with the method described in Journal of Biological Chemistry (J. Biol. Chem.) Vol. 234, page 2835 (1959). The results are shown in the following TABLE 1 in comparison with pravastatin.

TABLE 1

| Example | Compound No. | Compound | HMG-CoA Reductase Inhibition % ($10^{-7}$ M) |
|---|---|---|---|
| 3 | 8 | Sodium (E)-7-[4'-fluoro-5-(2-hydroxyothoxy)-3-(propan-2-yl)biphenyl-2-yl]-3,5-dihydroxy-6-heptenoate | 98 |
| 5 | 10 | Sodium (E)-7-[4'-fluoro-5-(2-methoxyethoxy)-3-(propan-2-yl)biphenyl-2-yl]-3,5-dihydroxy-6-heptenoate | 96 |
| 9 | 14 | sodium (E)-7-[4'-fluoro-3-(propan-2-yl)-5-(2-pyridylmethyloxy)biphenyl-2-yl]-3,5-dihydroxy-6-heptenoate | 95 |
| 11 | 16 | Sodium (E)-7-[4'-fluoro-3-(propan-2-yl)-5-(3-pyridylmethyloxy)biphenyl-2-yl]-3,5-dihydroxy-6-heptenoate | 95 |
| 13 | 18 | Sodium (E)-7-[4'-fluoro-3-(propan-2-yl)-5-(4-pyridylmethyloxy)biphenyl-2-yl]-3,5-dihydroxy-6-heptenoate | 96 |
| Reference Compound | | Pravastatin | 88 |

TEST 2

Determination of Inhibition of Sterol Synthesis

Representative compounds (0.3 mg/5 ml/kg) suspended in a 5% arabic gum solution were orally given to SD rate weighing 150 to 200 g.

Five hours later, ¹⁴C-acetic acid (100 μCi/kg) was intraperitoneally injected, and furthermore one hour later, liver was removed to determine the inhibitory activity of each of the compounds on the biosynthesis of sterol. The results are shown in comparison with simvastatin and pravastatin in TABLE 2.

TABLE 2

| Example | Compound No. | Compound | Administered Amount (mg/kg) | Sterol Synthesis Inhibition % |
|---|---|---|---|---|
| 3 | 8 | Sodium (E)-7-[4'-fluoro-5-(2-hydroxyethoxy)-3-(propan-2-yl)biphenyl-2-yl]-3,5-dihydroxy-6-heptenoate | 0.3 | 40 |
| 5 | 10 | Sodium (E)-7-[4'-fluoro-5-(2-methoxyethoxy)-3-(propan-2-yl)biphenyl-2-yl]-3,5-dihydroxy-6-heptenoate | 0.3 | 30 |
| Reference Compound 1 | | Pravastatin | 1 | 16 |
|  |  |  | 0.3 | — |
| Reference Compound 2 | | Simvastatin | 1 | 41 |
|  |  |  | 0.3 | 1 |

TEST 3

Determination of Partition Coefficient

The partition coefficient of each of representative compounds synthesized in the above-mentioned Examples was determined in accordance with the method by Hansh et al. (J. Am. Chem. Soc., 86, 5175 (1964)).

More specifically, the compound to be tested was dissolved in either an n-octanol solution which was saturated with a phosphoric acid buffer solution of pH 7.0 (Solution A) or a phosphoric acid buffer solution of pH 7.0 saturated with n-octanol (Solution B).

5 ml of the solution (Solution A or Solution B) in which the compound was dissolved and 5 ml of the solution (Solution B or Solution A) in which the compound was not dissolved were placed in a screw vial tube, and shaken for 30 minutes. This mixed solution was centrifuged for 15 minutes, and was then allowed to stand. The mixed solution was separated into two phases, that is, a water phase and a n-octanol phase.

The concentration of the compound in the water phase was determined by the UV method, and the concentration of the compound in the n-octanol phase was determined by deducting the concentration of the compound in the water phase from the concentration of the compound in the initially mixed solution (Solution A and Solution B).

The partition coefficient of the compound was calculated in accordance with the following formula:

$$\text{Partition coefficient } (P) = Co/Cw$$

wherein Co is the concentration of the compound in the n-octanol phase, and Cw is the concentration of the compound in the water phase.

The results of the partition coefficients of the tested compounds are shown in comparison with the partition coefficients of pravastatin and simvastatin in the following TABLE 3:

TABLE 3

| Example | Compound No. | Compound | Partition Coefficient |
|---|---|---|---|
| 3 | 8 | Sodium (E)-7-[4'-fluoro-5-(2-hydroxyethoxy)-3-(propan-2-yl)biphenyl-2-yl]-3,5-dihydroxy-6- | 1.3 |

TABLE 3-continued

| Example | Compound No. | Compound | Partition Coefficient |
|---|---|---|---|
| 5 | 10 | heptenoate<br>Sodium (E)-7-[4'-fluoro-5-(2-methoxyethoxy)-3-(propan-2-yl)biphenyl 2-yl]-3,5-dihydroxy-6-heptenoate | 5.2 |
| 7 | 12 | Sodium (E)-7-[4'-fluoro-5-[2-(2-methoxyethoxy ethoxy]-3-(propan-2-yl) biphenyl-2-yl]-3,5-dihydroxy-6-heptenoate | 3.3 |
| 9 | 14 | Sodium (E)-7-[4'-fluoro-3-(propan-2-yl)-5-(2-pyridylmethoxyloxy) biphenyl-2-yl]-3,5-dihydroxy-6-heptenoate | 27 |
| 11 | 16 | Sodium (E)-7-[4'-fluoro-3-(propan-2-yl]-5-(3-pyridylmethyloxy) biphenyl-2-dihydroxy-6-heptenoate | 26 |
| 13 | 18 | Sodium (E)-7-[4'-fluoro-3-(propan-2-yl)-5-(4-pyridylmethoxy) biphenyl-2-yl]-3,5-dihydroxy-6-heptenoate | 30 |
| Reference Compound 1 | | Pravastatin | 0.36 (0.34)[1] |
| Reference Compound 2 | | Simvastatin | 74[2] (75.8)[1] |

[1]Refered to JAMA (Japanese-Edition) October 1991 Supplement, pages 42–47.
[2]Determined in the form of a ring-opened type sodium salt.

The 4-fluorobiphenyl derivative of formula (I) has an inhibitory effect on the biosynthesis of cholesterol based on its inhibitory effect on HMG-CoA Reductase.

Furthermore, the partition coefficient of the 4-fluorobiphenyl derivative which indicates the degree of water solubility thereof is in the range of 1.2 to 30. In contrast to this, the partition coefficient of pravastatin is 0.36, and that of simvastatin is 74. Thus, the 4-fluorobiphenyl derivative of formula (I) has an appropriate water solubility, so that side effects such as myositis and sleep disorder are minimized. Furthermore, the 4-fluorobiphenyl derivative of formula (I) has an antiarteriosclerosis effect because of its cytostatic function with respect to the cells of smooth muscles and therefore is useful as an effective drug for curing arteriosclerosis.

Drugs comprising a 4-fluorobiphenyl derivative of formula (I) can be administered not only orally, but also through vena, by hypodermic injection, and by intramuscular injection. Therefore, these drugs can be used in the forms of a tablet, a capsule, a liquid, and a suppository.

What is claimed is:

1. A 4-fluorobiphenyl derivative of formula (I):

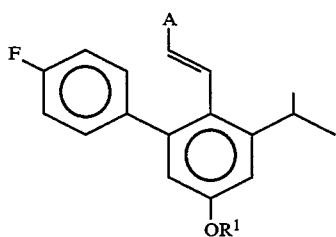

wherein A is a ω-oxycarbonyldihydroxybutyl group of formula (II):

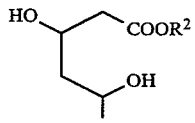

wherein $R^2$ is a hydrogen atom, an alkyl group having 1 to 6 carbon atoms, which may have a substituent, an alkaline metal or an alkaline earth metal; a tetrahydropyranyl group of formula (III):

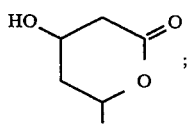

or a ω-oxycarbonyl-3-oxobutyl group of formula (IV):

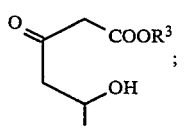

wherein $R^3$ is an alkyl group having 1 to 6 carbon atoms, which may have a substituent; $R^1$ is an alkyl group having 1 to 6 carbon atoms, which may have a substituent selected from the group consisting of a heteroaromatic group, an alkoxyl group having 1 to 6 carbon atoms, and a hydroxyl group.

2. The 4-fluorobiphenyl derivative as claimed in claim 1, wherein A is a ω-oxycarbonyldihydroxybutyl group of formula (II):

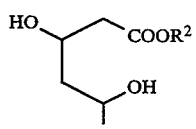

wherein $R^2$ is a hydrogen atom, an alkyl group having 1 to 6 carbon atoms, which may have a substituent, an alkaline metal or an alkaline earth metal.

3. The 4-fluorobiphenyl derivative as claimed in claim 1, wherein $R^1$ is an alkyl group having 1 to 6 carbon atoms, substituted with a heteroaromatic group.

4. The 4-fluorobiphenyl derivative as claimed in claim 1, wherein $R^1$ is an alkyl group having 1 to 6 carbon atoms, substituted with an alkoxyl group having 1 to 6 carbon atoms.

5. The 4-fluorobiphenyl derivative as claimed in claim 1, wherein $R^1$ is an alkyl group having 1 to 6 carbon atoms, substituted with a hydroxyl group.

6. A 4-fluorobiphenyl derivative of formula (IA):

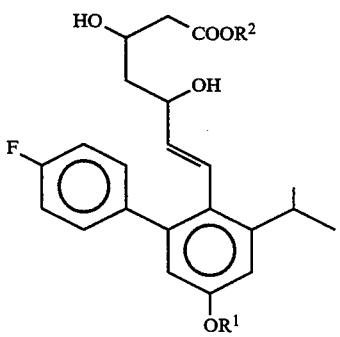

wherein $R^1$ is an alkyl group having 1 to 6 carbon atoms, which may have a substituent selected from the group consisting of a heteroaromatic group, an alkoxyl group having 1 to 6 carbon atoms, and a hydroxyl group; and $R^2$ is an alkaline metal.

7. The 4-fluorobiphenyl derivative as claimed in claim 6, wherein $R^1$ is an alkyl group having 1 to 6 carbon atoms, substituted with a heteroaromatic group.

8. The 4-fluorobiphenyl derivative as claimed in claim 6, wherein $R^1$ is an alkyl group having 1 to 6 carbon atoms, substituted with an alkoxyl group having 1 to 6 carbon atoms.

9. The 4-fluorobiphenyl derivative as claimed in claim 6, wherein $R^1$ is an alkyl group having 1 to 6 carbon atoms, substituted with a hydroxyl group.

10. A cholesterol or lipid lowering agent comprising a 4-fluorobiphenyl derivative of formula (IB) as an effective component:

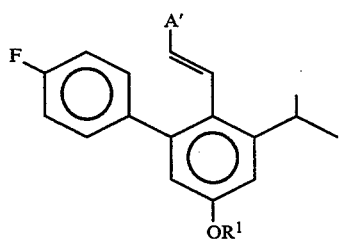

wherein A' is a ω-oxycarbonyldihydroxybutyl group of formula (II):

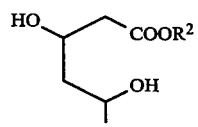 (II)

wherein $R^2$ is a hydrogen atom, an alkyl group having 1 to 6 carbon atoms, which may have a substitutent, an alkaline metal or an alkaline earth metal; a tetrahydropyranyl group of formula (III):

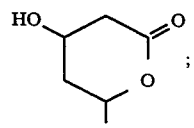 (III)

$R^1$ is an alkyl group having 1 to 6 carbon atoms, which may have a substituent selected from the group consisting of a heteroaromatic group, an alkoxyl group having 1 to 6 carbon atoms, and a hydroxyl group.

11. The cholesterol or lipid lowering agent as claimed in claim 10, wherein A' is a ω-oxycarbonyldihydroxybutyl group of formula (II):

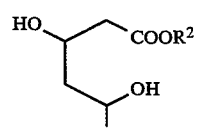 (II)

wherein $R^2$ is a hydrogen atom, an alkyl group having 1 to 6 carbon atoms, which may have a substitutent, an alkaline metal or an alkaline earth metal.

12. The cholesterol or lipid lowering agent as claimed in claim 10, wherein $R^1$ is an alkyl group having 1 to 6 carbon atoms, substituted with a heteroaromatic group.

13. The cholesterol or lipid lowering agent as claimed in claim 10, wherein $R^1$ is an alkyl group having 1 to 6 carbon atoms, substituted with an alkoxyl group having 1 to 6 carbon atoms.

14. The cholesterol or lipid lowering agent as claimed in claim 10, wherein $R^1$ is an alkyl group having 1 to 6 carbon atoms, substituted with a hydroxyl group.

15. A cholesterol or lipid lowering agent comprising a 4-fluorobiphenyl derivative of formula (IA) as an effective component:

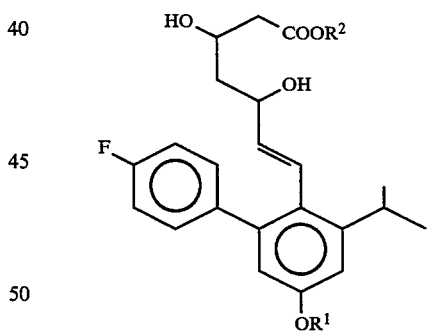

wherein $R^1$ is an alkyl group having 1 to 6 carbon atoms, which may have a substituent selected from the group consisting of a heteroaromatic group, an alkoxyl group having 1 to 6 carbon atoms, and a hydroxyl group; and $R^2$ is an alkaline metal.

16. The cholesterol or lipid lowering agent as claimed in claim 15, wherein $R^1$ is an alkyl group having 1 to 6 carbon atoms, substituted with an alkoxyl group having 1 to 6 carbon atoms.

17. The cholesterol or lipid lowering agent as claimed in claim 15, wherein $R^1$ is an alkyl group having 1 to 6 carbon atoms, substituted with a hydroxyl group.

18. The cholesterol or lipid lowering agent as claimed in claim 15, wherein $R^1$ is an alkyl group having 1 to 6 carbon atoms, substituted with a heteroaromatic group.

* * * * *

UNITED STATES PATENT AND TRADEMARK OFFICE
CERTIFICATE OF CORRECTION

PATENT NO. : 5,393,780
DATED : February 28, 1995
INVENTOR(S) : Masakatsu MATSUMOTO, ET AL.

It is certified that error appears in the above-identified patent and that said Letters Patent is hereby corrected as shown below:

Column 1, line 65, "ML-235B" should read --ML-236B--.

Column 2, line 16, "German Laid-Open Patent 3909278"
          should read --German Laid-Open Patent 390378--.

Column 10, line 67, "group." should read --group--.

Column 16, line 39, "0.05 ml" should read --0.5 ml--.

Signed and Sealed this

Twenty-sixth Day of March, 1996

*Attest:*

BRUCE LEHMAN

*Attesting Officer*    Commissioner of Patents and Trademarks